(12) United States Patent
Kreger et al.

(10) Patent No.: US 8,923,918 B2
(45) Date of Patent: Dec. 30, 2014

(54) BIOSENSOR INTERFACE APPARATUS FOR A MOBILE COMMUNICATION DEVICE

(75) Inventors: Kevin Kreger, Milwaukee, WI (US); Gajanan Nagarsekar, Milwaukee, WI (US)

(73) Assignee: Kallows Engineering India Pvt. Ltd., Goa (IN)

( * ) Notice: Subject to any disclaimer, the term of this patent is extended or adjusted under 35 U.S.C. 154(b) by 128 days.

(21) Appl. No.: 12/972,470

(22) Filed: Dec. 18, 2010

(65) Prior Publication Data

US 2012/0156933 A1   Jun. 21, 2012

(51) Int. Cl.
| | |
|---|---|
| *H04M 1/00* | (2006.01) |
| *A61B 5/024* | (2006.01) |
| *A61B 5/0245* | (2006.01) |
| *A61B 5/11* | (2006.01) |
| *A61B 5/1455* | (2006.01) |
| *A61B 5/00* | (2006.01) |
| *G01N 33/487* | (2006.01) |

(52) U.S. Cl.
CPC ............ *A61B 5/02433* (2013.01); *A61B 5/0245* (2013.01); *A61B 5/1118* (2013.01); *A61B 5/14552* (2013.01); *A61B 5/6898* (2013.01); *A61B 5/6803* (2013.01); *A61B 5/6806* (2013.01); *A61B 5/6816* (2013.01); *A61B 5/6823* (2013.01); *A61B 5/6824* (2013.01); *A61B 5/6825* (2013.01); *G01N 33/48792* (2013.01)

USPC ................... 455/556.1; 455/554.2; 455/556.2

(58) Field of Classification Search
CPC ........................................................ G06F 3/00
USPC .......... 455/67.11, 456.3, 550.1, 554.2, 556.1, 455/556.2
See application file for complete search history.

(56) References Cited

U.S. PATENT DOCUMENTS

| | | | |
|---|---|---|---|
| 6,725,092 B2 * | 4/2004 | MacDonald et al. ............. 607/2 |
| 7,438,410 B1 | 10/2008 | Howell et al. |
| 2004/0157546 A1 * | 8/2004 | Fantaay ....................... 455/3.03 |
| 2005/0049515 A1 | 3/2005 | Misczynski et al. |
| 2007/0055738 A1 | 3/2007 | Nakamoto et al. |
| 2010/0056956 A1 * | 3/2010 | Dufresne et al. ............. 600/586 |
| 2012/0001751 A1 * | 1/2012 | Baker et al. ............. 340/539.12 |
| 2012/0022886 A1 * | 1/2012 | Ohnemus .......................... 705/2 |
| 2012/0271559 A1 * | 10/2012 | Carpenter et al. ............. 702/19 |

FOREIGN PATENT DOCUMENTS

EP          1 475 035          10/2004

* cited by examiner

*Primary Examiner* — Tuan H Nguyen
(74) *Attorney, Agent, or Firm* — Boyle Fredrickson, S.C.

(57) ABSTRACT

A biosensor interface apparatus that utilizes pre-existing or standard electrical connectors of mobile devices such as smart phones, mobile media players, and tablets. The interface device transforms the input biosensor signals to compatible electrical signals for input to one or more of the mobile's connectors. That signals are then conducted via one or more input conductors in the connectors to the mobile's microprocessor, which may display or transmit the biosensor signals and derive further measurements from them.

19 Claims, 22 Drawing Sheets

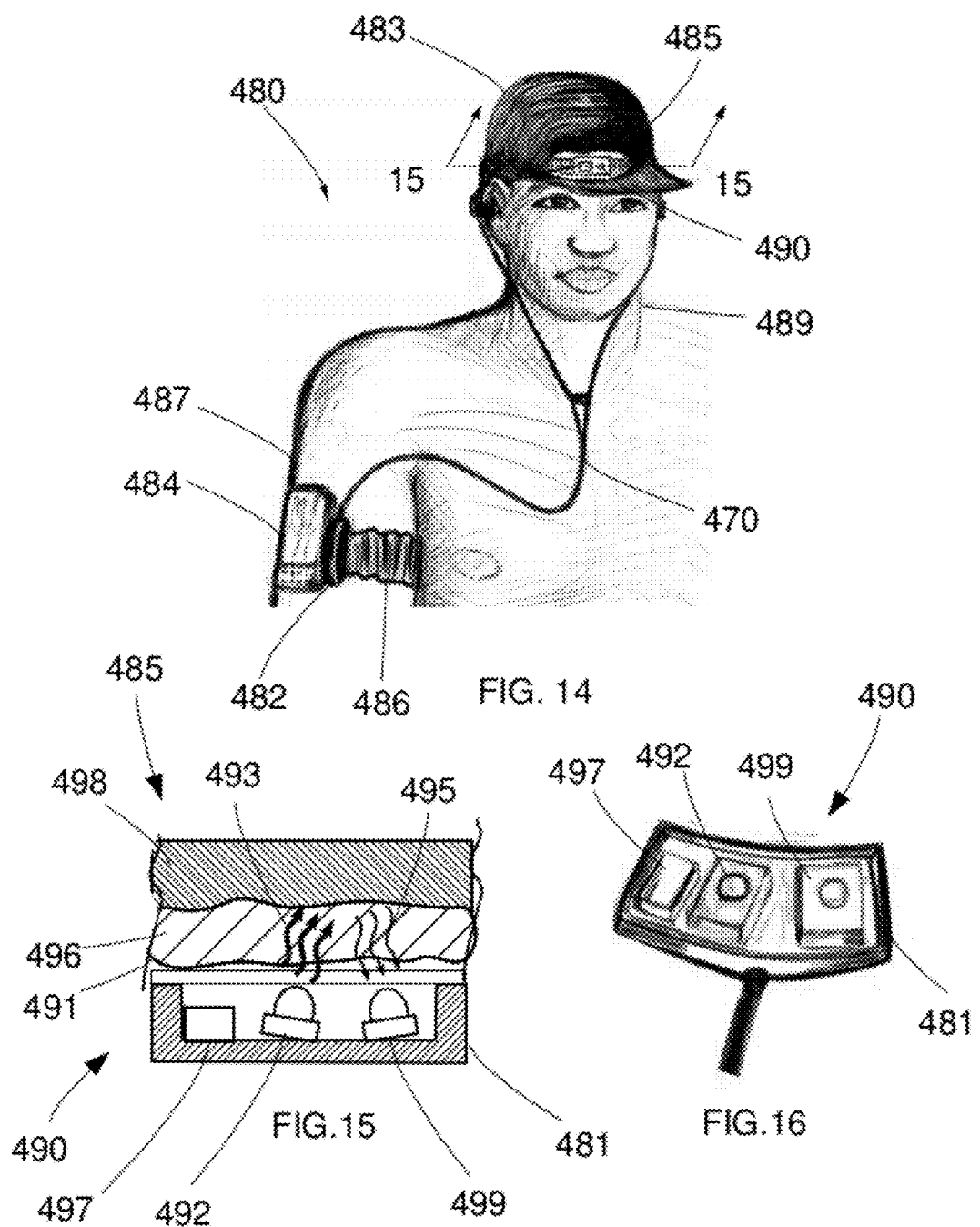

BIOSENSOR INTERFACE APPARATUS FOR A MOBILE COMMUNICATION DEVICE

BACKGROUND OF THE INVENTION

1. Field of the Invention

The present invention pertains to biosensors that connect to a mobile communications device ("mobile"), such as a smart phone or portable media player, and more particularly, the present invention pertains to improvements to interfacing one or more biosensors to a mobile using the mobile's existing connectors.

2. Discussion of the Related Art

In light of numerous concerns, many biosensor signals are preferably conducted or transmitted with electrical conductors such as wires, pins, connectors, and traces rather than wirelessly. For example, hospitals may prohibit certain RF producing devices because they may produce unsafe interference with other medical equipment. Another concern is the contamination of the biosensor signal with noise during the RF transmission process. Yet another important concern is the security of the medical information that may be broadcast wirelessly.

As well, wireless requires additional power versus a wired connection. Reduction in power consumption can allow longer usage times, smaller batteries, and less time spent recharging the device. Bio sensor availability is certainly a concern for a fitness enthusiast that loses power to her biosensor monitor in the middle of a workout, however, it is a major concern for medical personnel who may lose a biosensor while monitoring a critical patient in the field.

Another concern is producing a green product that minimizes environmental impact. A device that is wireless consumes more power potentially creating a larger carbon footprint. A wireless device also broadcasts RF which is a source of electromagnetic noise and a potential health concern for humans and wildlife.

Finally, cost is a major concern, especially for medical care personnel in remote areas who would most benefit from the integration of a low-cost mobile communication device with a biosensor.

What is needed is then is an interface apparatus for a mobile that utilizes existing hard-wired interface connectors that are common to many mobiles. Thus, the mobile serves as the biosensor monitor, saving cost, and also allowing the advantages of a wired biosensor connection.

SUMMARY OF THE INVENTION

Mobile device technology has continuously improved in terms of processing power, storage capabilities, data transmission, and so forth. For example, modern smart phones are capable of providing complex application support for biosensors by allowing storage, display, calculation of health parameters, and communication of the biosensor data from remote locations.

The present invention acts as an interface apparatus for various biosensors to utilize the electrical connectors of a mobile, such as a smart phone, so that the mobile becomes the heart of the biosensor monitoring system, either for sports/fitness or medical applications. Thus, the interface device receives at least one biosensor signal and has one or more mating connectors which mate with the mobile's electrical connectors. The electrical connector has a plurality of conductors with one or more of the conductors providing an input in communication with a mobile's processor. The interface device transforms the received biosensor signals to compatible electrical signals for the connectors' inputs.

In one embodiment the biosensor interface apparatus may comprise a power source, a mobile communications device with an electrical connector with a plurality of conductors (where there is an input conductor in communication with a mobile communications device processor), and an interface device in communication with at least one biosensor signal. Notably, the interface device has one or more mating connectors configured to be mechanically received by corresponding electrical connectors on the mobile communications device. The interface device transforms the biosensor signals to compatible electrical signals that are receivable by one or more input conductors and communicated to the mobile's processor.

Thus, it is one object of the apparatus to provide a simple, inexpensive device for monitoring biosensors that utilizes the smart phone and its associated capabilities including its processing power and the data input capabilities of its electrical connectors.

In alternative embodiments the mobile communication device may be a mobile phone, a personal digital assistant, a smartphone, a portable media playback device, a handheld tablet, and the like. Thus, it is one object of the device to provide for an flexible interface apparatus that will be compatible with a variety of mobile communications devices.

In another aspect of this embodiment, the mobile's electrical connector is an audio connector configured to receive an electrical audio signal. For example, the audio connector may have one more input conductors such as microphone level input conductors, and audio recording line level input conductors. The corresponding interface device mating connector may be analog audio connectors, for example: a male 2.5 mm 3-conductor plug, a male 2.5 mm 4-conductor plug, a male 3.5 mm 3-conductor plug, a male 3.5 mm 4-conductor, a manufacturer specified stereo recording input plug or plugs, a manufacturer specified headset connector, and a manufacturer specified microphone connector.

Thus, one object of the interface apparatus is to provide for biosensor signals to be received by the mobile's microphone and/or line level inputs (either stereo or monaural) thereby using the filters and analog to digital converters of those existing inputs as well as the processing, display, and so forth, of the mobile.

In one aspect of this embodiment the electrical connector is a hybrid connector configured to receive serial data and to receive at least one electrical audio signal. In another aspect of the biosensor interface apparatus the electrical connector is a serial connector configured to receive serial data. In yet another aspect the electrical connectors that are utilized are some combination of an audio connector, a serial connector, and a hybrid connector.

Thus the corresponding mating connectors of the interface device may be: an Apple® iPod® media player and iPhone® 30 pin connector; an Audiovox® cell phone 22 24, or 26 pin connector; an Ericsson® cell phone 10 pin connector; a Kyocera® cell phone and MP3 player 16 pin connector; a Motorola® cell phone 4, 5, 15, 17, and 26 pin connector; a Nokia® cell phone 14 pin connector; a Qualcomm® cell phone 15 pin connector; a Samsung® Cell Phone and PDA 5 or 19 pin connector; a Sanyo® cell phone 16 or 18 pin connector; a Siemens® cell phone 12 pin connector; a 4-pin electrically compatible USB connector; and a manufacturer specified docking connector.

As well, for serial and some hybrid connections, the interface device mating connector may be a USB Mini-A, USB Mini-B, USB Micro-AB, USB Micro-B, USB Type A, USB Type B, and a 4-pin electrically compatible USB connector having a non-standard connector or housing.

Thus, one object of the invention is to provide compatible mating connectors to a mobile's electrical connectors, including connectors that double as a headset and data connector, a docking connector, a serial connector, an audio connector, a headset connector, and the like.

In one aspect of this embodiment the interface device transforms the received biosensor signals to compatible electrical signals for the connectors' inputs by one or more of the following: DC voltage cancellation, filtration, attenuation, demodulation, modulation, compression, amplification, expansion, digitization, serialization, demultiplex, multiplex, switching, synchronization, electrical isolation, and impedance matching.

Thus, it is another object to provide compatible signals to the mobile's electrical connectors which may involve transforming the biosensor signals to match requisite impedance and signal levels, eliminate noise, cancel DC noise and drift, demultiplex or multiplex multiple measurements, provide electrical isolation, serialization, synchronization, and so forth.

In one aspect of another embodiment, the biosensor interface apparatus further includes one or more biosensors. The biosensors may be electrodes including ECG electrodes, a photo plethysmograph (PPG), a pulse oximeter, a sphygmomanometer (inflatable blood pressure cuff), a thermometer/temperature sensor, a pedometer, a capnograph, a respiratory movement sensor, a respiratory flow sensor, a transdermal blood alcohol sensor, and a blood sugar sensor (glucometer). Thus it is an object to provide for a wide range of common medical and sport/fitness biosensors in a single compact interface apparatus.

In one aspect of another embodiment, the biosensor interface apparatus further includes one or more biosensor connectors capable of receiving a biosensor signal. Thus it is an object to provide an interface apparatus that supports biosensors' industry standard and manufacturer specified probe connectors, thereby improving the invention's usability and promoting reuse of existing biosensor probes.

In one aspect of another embodiment, the biosensor interface apparatus further includes at least one connector capable of receiving a biosensor signal, wherein the biosensor signal is an electrical signal, a chemical signal, a gas signal, or a force signal. Thus, it is one object to provide for transmission of gas, chemical compounds, or force such as through a tube in order to measure, for example, end-tidal $CO_2$ ($ETCO_2$), respiratory rate (RR), or respiratory flow with a capnograph. It is another object to provide for the transmission of an electrical signal such as from an ECG or pulse oximeter. In addition vibrations and other audible and inaudible force may be detected by a force sensor that could be in communication with a stethoscope or accelerometer.

In one aspect of another embodiment, the biosensor interface apparatus further includes at least one connector capable of receiving a biosensor signal, such as a circular push-pull connector, an ECG AAMI EC-53 connector, a MC PPG connector; a round connector, a screw connector, a rectangular (DIN) connector, a twist coupling connector, a sub-miniature connector, and other industry specified connectors. Thus, it is an object to provide for multiple biosensor probe connectors thereby supporting a wider range of existing biosensors.

In one aspect of yet another embodiment the power source is within the mobile communication device, and the interface device further comprises a power connection to the mobile communication device. Thus, it is one object of the invention to utilize power provided through the mobile's electrical connectors to minimize the cost and complexity of the present invention.

In an aspect of another embodiment the biosensor interface apparatus includes a mobile communication device processor that computes a physiological measurement corresponding to the electrical signal received from one or more input conductors, the processor also communicates measurements to an audio output device and a display. In another aspect of the present invention the display may also include a video device connected to the mobile device's HDMI or other video connector.

Thus, it is one object of the present invention to utilize the audio-visual and processing capabilities of the mobile to present biosensor data such as plots and measurement visually on the display and audibly with the audio output device (such as a user's headset).

These and other aspects and objects of the present invention will be better appreciated and understood when considered in conjunction with the following description and the accompanying drawings. It should be understood, however, that the following description while indicating preferred embodiments of the present invention is given by way of illustration and not of limitation. Many changes and modifications may be made within the scope of the present invention without departing from the spirit thereof, and the invention includes all such modifications.

BRIEF DESCRIPTION OF THE DRAWINGS

Preferred exemplary embodiments of the invention are illustrated in the accompanying drawings in which like reference numerals represent like parts throughout, and in which:

FIG. 14 is front elevational view of another embodiment having a PPG worn on the forehead and a sphygmomanometer worn on the upper arm;

FIG. 15 is a cross-section view of the PPG of FIG. 14 taken along the 15 axes;

FIG. 16 is a bottom elevational view of the PPG of FIG. 14;

DETAILED DESCRIPTION OF THE EMBODIMENTS

Figure 1:
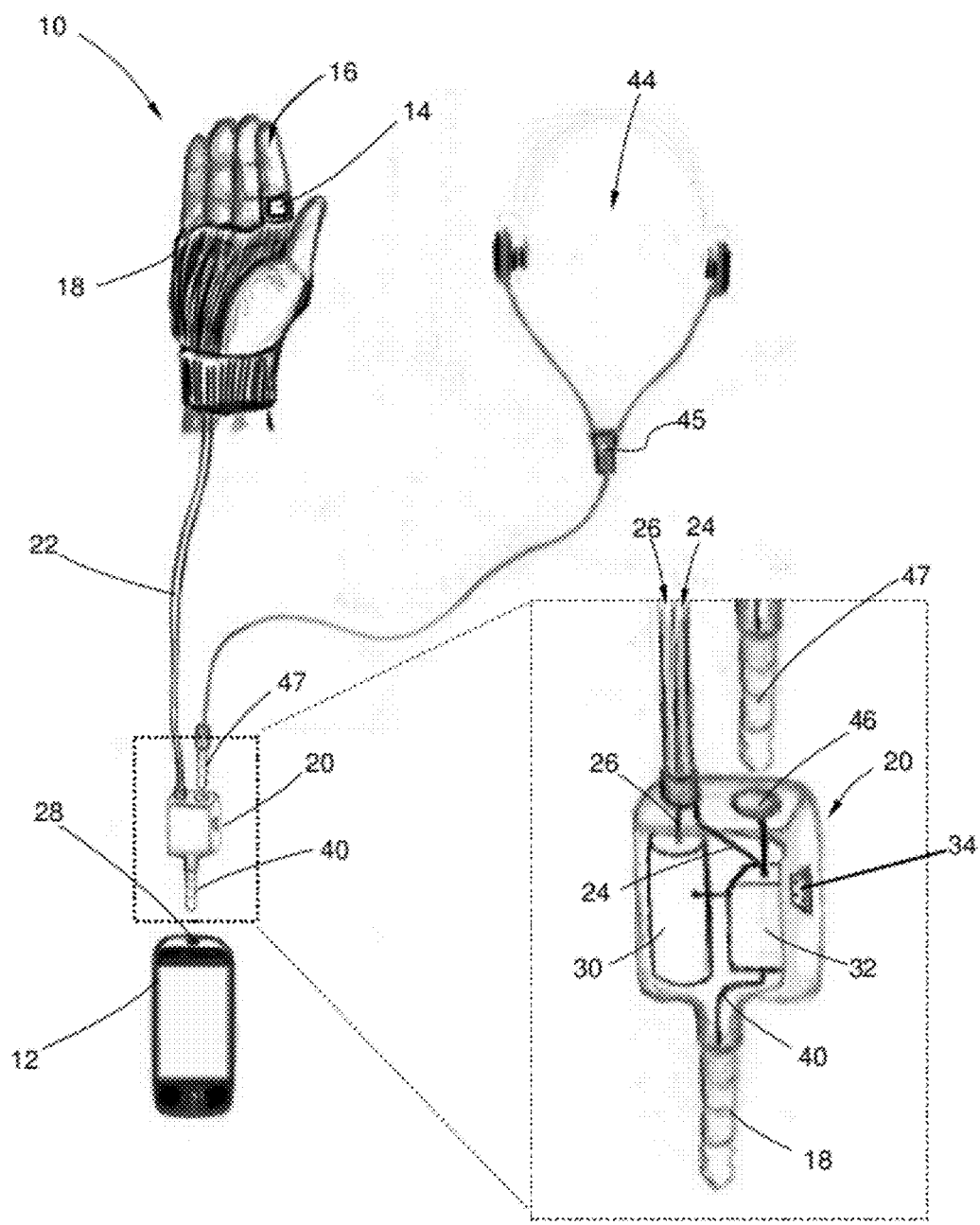
FIG. 1 is a side elevational view of an embodiment of the biosensor interface apparatus of the present invention with a close-up inset view.

With reference to FIG. 1, there is shown a first embodiment of the biosensor interface apparatus for use with a mobile communication device 10. The biosensor 14 produces one or more biosensor signals transmitted via cable 22 and received by interface device 20. The interface device transforms the biosensor signals so that they can be conducted via electrical connector 28 and compatibly received by the mobile communications device shown as smart phone 12.

In other embodiments, the mobile communications device can be any of a number of mobile phones such as an iPhone® or an Android® phone, a personal digital assistant (PDA) such as a Blackberry®, a portable audio playback device such as an MP3 player, a portable media playback device such as an iPod®, or a handheld tablet such as an iPad®.

Continuing with FIG. 1, the biosensor is shown as a pulse oximeter 14 in communication with finger 16. The pulse oximeter may provide a pulse signal to calculate BPM, a $SPO_2$ reading, or a diagnostic cardiac waveform. The pulse oximeter 14 may be retained against the base of finger 16 using a mounting device that may be worn on the finger or hand, shown as gauntlet 18. Alternatively, the pulse oximeter may be worn on the fingertip, ear, forehead, or nasal septum using various mounting devices such as rings, clips, elastic straps, and adhesive pads.

Figure 2:
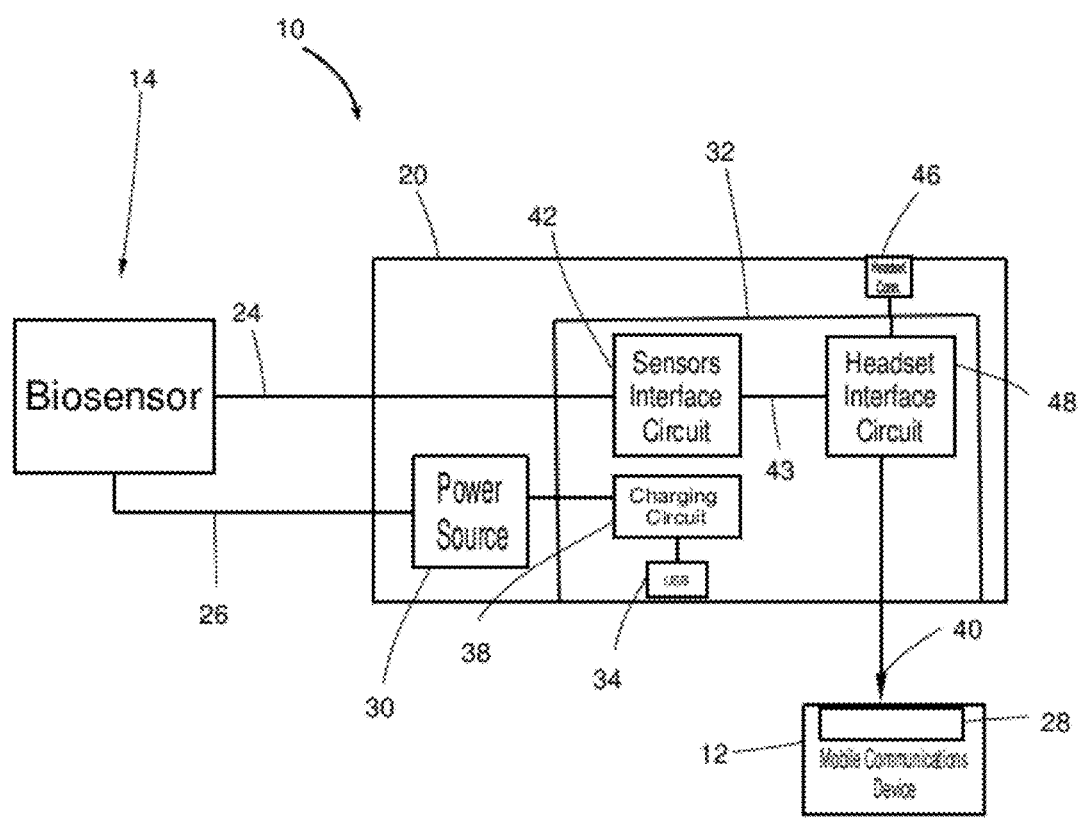
FIG. 2 is a block diagram of the embodiment of FIG. 1.

Referring to FIGS. 1 and 2, the biosensor 14 may be in communication with the interface device 20 via cable 22. The cable may contain one or more conductors 24, 26. The cable 22 may transmit power to the pulse oximeter 14 via conductor 26, or may transmit biosensor signals, such as the two absorption light signals from the pulse oximeter 14, via conductor 24.

The interface device 20 may have a power source 30 and a circuit assembly 32. Interface device 20 may have a power source shown as battery 30 in communication with conductor 26. Interface device 20 may also contain circuit assembly 32 which may have a charging circuit 38, a sensors interface circuit 42 and a headset interface circuit 48 described below.

Continuing with FIGS. 1 and 2, the interface device circuit assembly 32 may have a charging circuit 38 having an interface to a connector shown as USB connector 34 that can provide power to charge battery 30 via conductor 36. As well the USB connector 34 may provide data communications. The interface device 20 may also provide a mating connector shown as four conductor male audio plug 40. The audio plug 40 mechanically mates with an electrical connector on the mobile phone 12 shown as female audio plug receptacle 28. The plug receptacle 28 contains one or more input conductors that communicate the biosensor signals to the mobile's microprocessor as will be described below.

The interface device 20 may also provide a sensors interface circuit 42 which receives biosensor signals on input conductor 24 and transforms the signals to output electrical signals 43 that are output on electrical connector 28. The interface circuit provides output electrical signals 43 signals that are electrically compatible, for example, with respect to impedance, voltage amplitude, noise levels, and so forth such that the signals can be received by the mobile's processor via connector 24.

Continuing with FIGS. 1 and 2, the interface device 20 may also contain a headset interface circuit to support the connection of headset 44 to mobile 12. The headset interface circuit 48 connects to headset 44 having audio plug 47 via a replacement electrical connector shown as female audio plug receptacle 46. The replacement electrical connector 46 replaces the electrical connector 28 (which the interface device 20 is engaging) thereby allowing the user's headset 44 to be connected along with the biosensor interface apparatus 10. The headset 44 may have a switch 45 allowing the user to initiate or answer a phone call while using the biosensor interface device 10. Thus, the headset interface circuit 48 may control the connections made to the mobile's electrical connector 28. For example, the headset interface circuit 48 may connect the headset 44 or the sensors interface circuit biosensor outputs 50 to connector 28. Alternatively, the headset interface circuit 48 could multiplex the connection of both the headset 44 and the sensors interface circuit's output electrical signals 43. As mentioned above, the operation of the headset interface circuit 48 could be under user control, for example with switch 45, or under automatic control, for example, in the case of an incoming call. For example, the incoming call may automatically switch the microphone input from the biosensors to the headset microphone.

Figure 3:
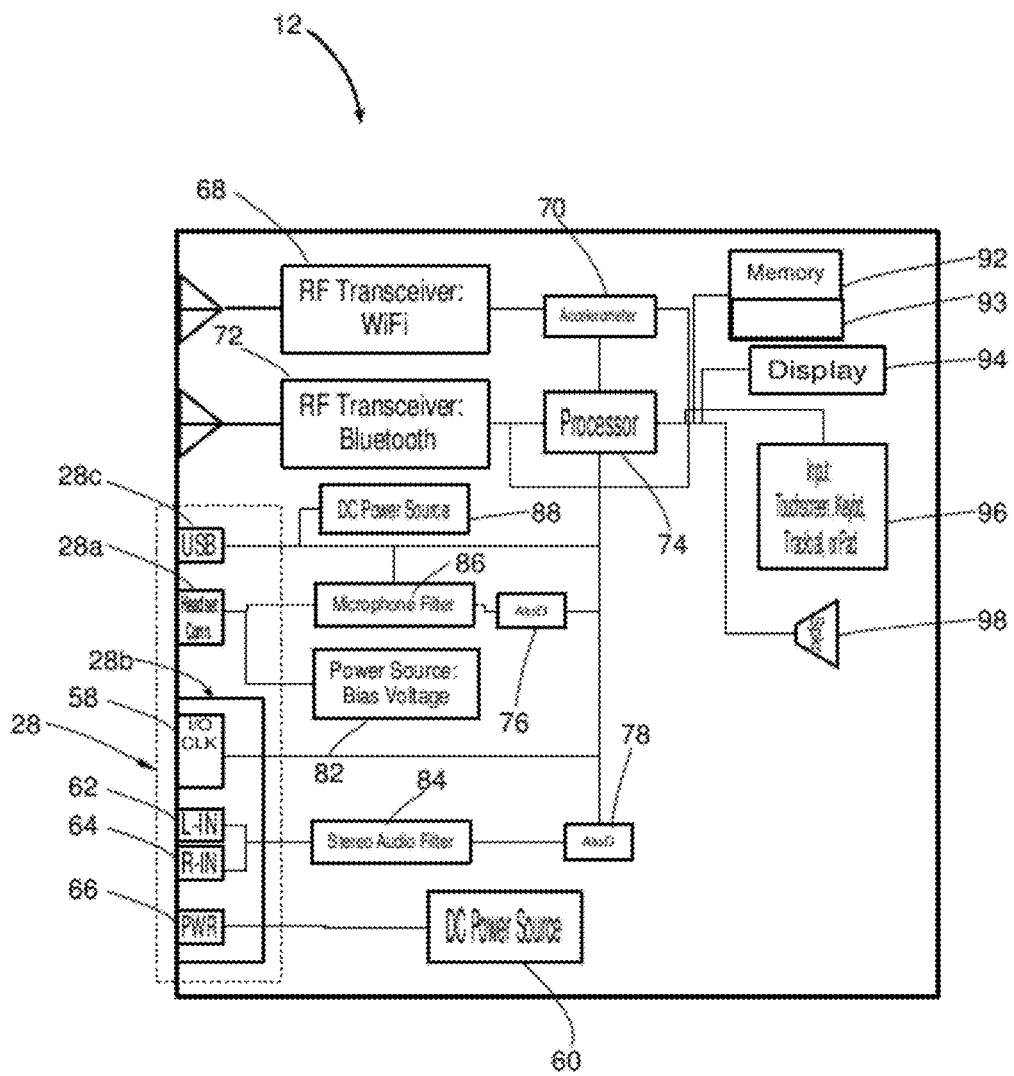
FIG. 3 is a block diagram of a mobile communications device.

Turning now to FIG. 3, a mobile communications device 12 of the present invention is shown as a block diagram. The biosensor signals may be received by one or more electrical connectors 28 on the mobile 12 and communicated to the processor 16 whereupon the microprocessor produces a biosensor measurement or a biosensor signal for analysis. The electrical connectors 28 are shown as a headset audio connector 28a (providing a microphone input and at least one audio output); a hybrid power, data and audio connector 28b (aka docking connector); and USB connector 28c. Although the USB connector 28c may provide data communications, it may also double as a headset connector. The docking connector 28b may be comprised of connections that allow recording high quality with audio inputs 62, 64; provide a source of DC power 60 via power connection 66; and provide other data input/output ("I/O") via I/O and clock connections 58.

Continuing with FIG. 3, analog input signals received by mobile 12 are digitized and communicated to the processor 74. The headset inputs from the headset connector 28*a*, the USB connector 28*c*, and the docking connector 28*b* (not shown) may be filtered by microphone filter, undergo analog to digital conversion using analog to digital ("AtoD") 76, and be communicated to the microprocessor 74. In addition, the audio inputs, generally for high-quality stereo 62, 64 may be filtered by stereo audio filter 84 (such as an anti-aliasing filter) and then digitized by AtoD 78 and communicated to the microprocessor 74. Alternatively, the audio filter 84 and the AtoD 78 could be integrated, and the microphone filter 86 and the AtoD 76 may be combined such as in a CODEC (not shown). In addition, data input signals received by mobile 12 may be communicated to microprocessor 74 from USB connector 28*c*, and the data I/O connections 58 of docking connector 28*b*. The data connections can be serial or parallel, asynchronous or synchronous, and may comprise clock signals. Alternatively, the audio inputs 62, 65 may be separate female audio connectors rather than in a docking connector 28*b*.

Continuing to refer to FIG. 3, the microprocessor 74 receives one or more biosensor signals and may transform the data into a biosensor measurement such as BPM, or an otherwise useful signal such as a ECG signal suitable for medical diagnosis. The signals and measurements may be stored in memory 12 and may be used for plotting on display 94. The signals and measurements may also be used to provide information such as a BPM via speaker 98 or via a headset or earpiece (not shown). In addition, biosensor data may be produced by the mobile's internal accelerometer 70 if it is in communication with a human body, thereby serving as a biosensor that may be used to determine the patient's position, respiratory movement, and so forth.

The sensor data and measurements may be transmitted to remote medical personnel, internet servers, and others using WiFi transceiver 68, Bluetooth transceiver 72 or other RF transmitter such as for a cellular phone network. As well, the signals and measurements on the mobile 12 may be transferred via a cable connected to USB connector 28*c* or docking connector 28*b* to another computer storage device, over a computer network, to a personal computer, and so forth.

Figures 4A, 4B:
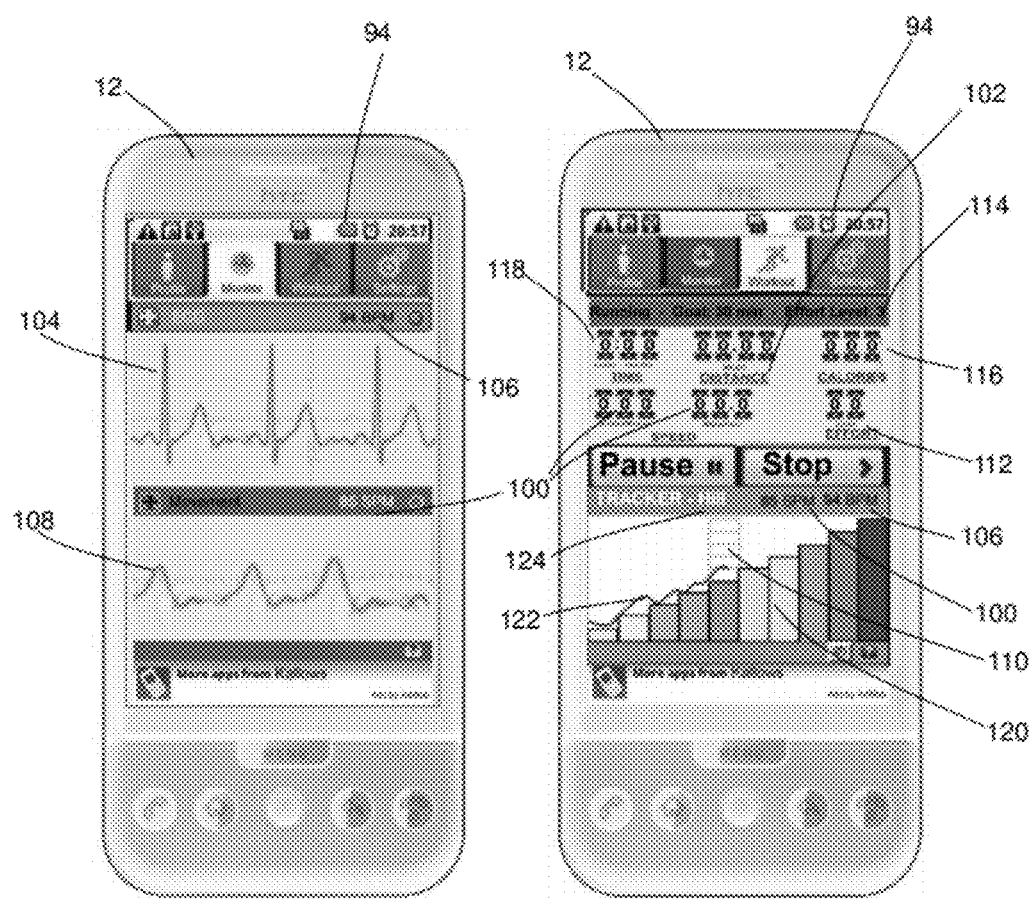
FIGS. 4a and 4b are screen shots of the mobile communications device having a biosensor monitoring application running.

Referring now to FIGS. 4*a* and 4*b* and also to FIG. 3, the microprocessor 74 may drive a display 94 to display the biosensor signals and measurements derived there from. For example a movement sensor may be used to determine the speed 100 (strides per minute or SPM) or distance traveled 102 by an athlete during a workout. A cardiac sensor my provide an ECG signal 104 which can be used to calculate the heart rate 106. The speed 100 can be used separately, but preferably in tandem, to perform a cardiac stress exam and determine a patient's stress level. Speed 100 and/or heart rate 106 may also be used to monitor and control an effort level 110, 112 in a workout. As well, effort level 114 may be a target that is set for the workout. Goals may be set and measurements may be displayed on, for example, a workout timer 112, which may show elapsed or remaining time and may have controls to set workout time. Moreover, other measurements such as Calories 116 may be displayed as "Calories elapsed" or "Calories remaining until goal". Similarly for elapsed or remaining distance 102, a distance goal can be set, for example, in strides, miles, or kilometers. As well, for effort where an actual effort level 122 and a target effort level 120 can be shown graphically and the user may choose a certain effort profile or course such as Hill 124.

Figure 5:
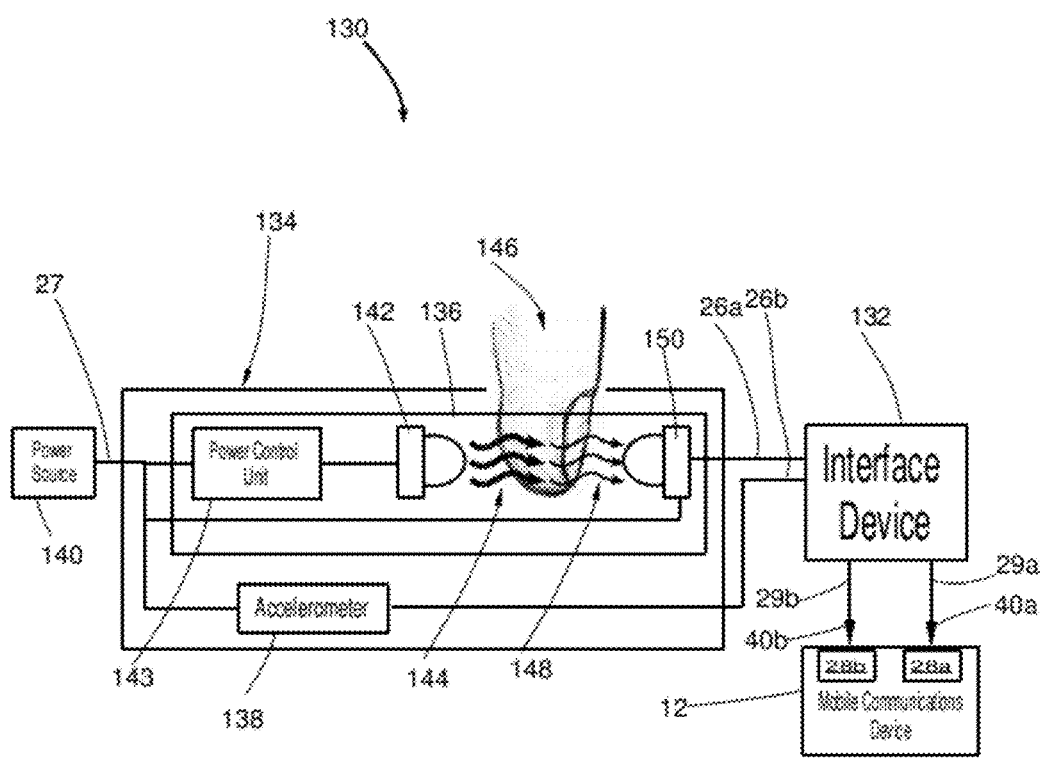
FIG. 5 is a block diagram of another embodiment of the present invention having a photo plethysmograph and an accelerometer.

Turning now to FIG. 5, an embodiment of the present invention 130 has a interface device 132 permitting sensor assembly 134 to connect to mobile 12 with mating connectors audio connector 29*a* and docking connector 29*b* which are connected to the mobile's corresponding electrical connectors audio connector 28*a* and docking connector 28*b*.

The sensor assembly 134 has a cardiac sensor shown as photo plethysmograph ("PPG") 136, a movement sensor accelerometer 138, and an external power source 140 supplying power to both sensors via power connection 27. The PPG 136 works as follows: first, an infrared ("IR") light emitting diode ("LED") 142 has power applied by power control unit 143 thereby stimulating it to emit IR light 144, some of which is scattered, reflected or absorbed by a human tissue such as finger 146. Next, some light 148 emerges from finger 146 striking an infrared sensor such as photodiode 150. The photodiode electrical output (i.e. the PPG signal having pulsatile blood flow) is communicated to interface device 132 via connection 26*a*, while one or more accelerometer signals are communicated to the interface device 132 via connection 26*b*. Note that 26*a*, 26*b* may be hardwired as shown or releaseably connected to interface device with mating connectors (not shown).

Figure 6:
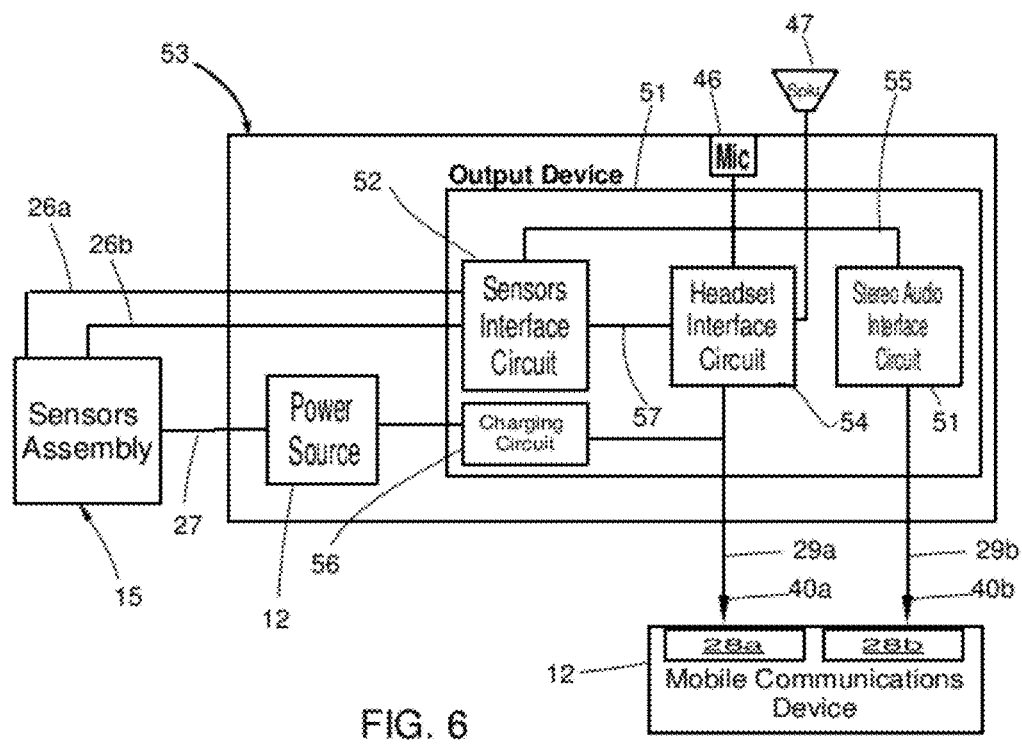
FIG. 6 is a block diagram of yet another embodiment of the present invention having multiple biosensor and multiple audio mating connectors.
Figure 7:
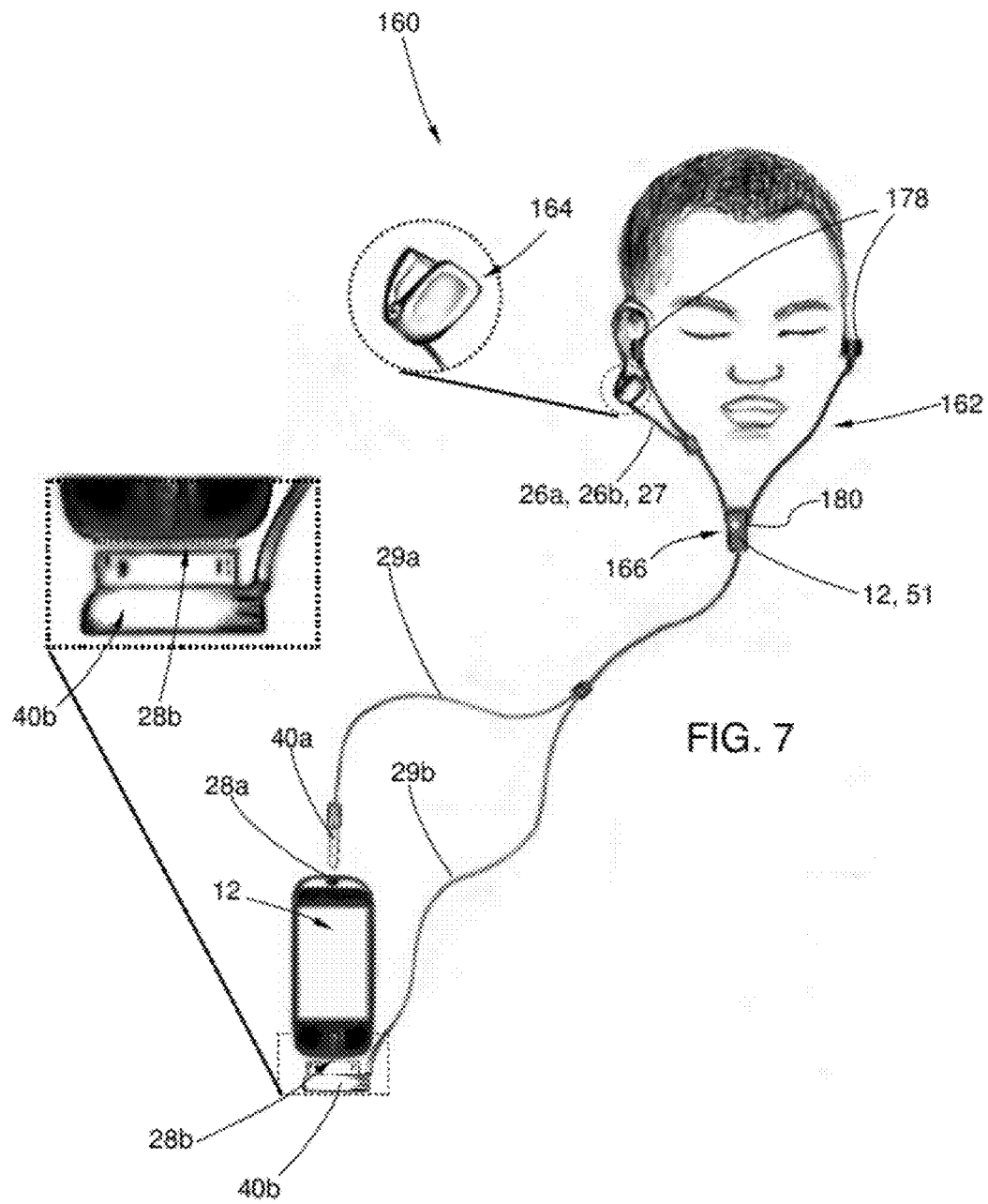
FIG. 7 is a side elevational view of the embodiment of FIG. 6 having a photo plethysmograph worn on an earlobe, mating connectors for headset and dock, and an integrated headset.

Turning now to FIGS. 6 and 7, an embodiment of the biosensor interface apparatus 160 may be integrated into a mobile headset 162 having speakers 178 for the ear and a microphone 180, but also having a sensors assembly 164. The sensors assembly 164 may have a cardiac sensor and a movement sensor, for example, a PPG and an accelerometer. In this embodiment the sensors assembly 164 receives power from and communicates signals to the interface device 166 as follows: PPG signal on conductor 26*a*, one or more accelerometer signals on conductors 26*b*, and power on conductor 27. Furthermore, power source 168 on interface device 166, which supplies power on conductor 27, may also supply power to the other circuits on the interface device 166, and may receive power via power charging circuit 170. Power charging circuit 170 may receive power from mobile communications device 12, for example, from a microphone bias voltage via headset connector 28*a*, or from a power source on docking connector 28*b*. In alternative embodiments the power source 168 may be external or it may be within mobile 12, sensors assembly 164, and/or interface device 166.

The interface device 166 receives the sensors signals 26*a*, 26*b* with sensors interface circuit 172. The sensors interface circuit may convert and condition the sensors signals 26*a*, 26*b* and produce electrical signals 174*a*, 174*b* for subsequent input to a respective electrical connector 28*a*, 28*b* on the mobile 12.

The electrical PPG signal 174*a* is communicated to headset interface circuit 176, which may further condition the signal, for example to match an electrical circuit impedance. As well, the headset interface circuit connects or switches the resulting signal to output conductor 29*a*. The headset interface circuit may also connect the headset speakers 178 and microphone 180 to output conductor 29*a*. The headset interface circuit may also combine or multiplex the microphone signal 182 and the PPG signal 174*a* to output conductor 29*a*.

Similarly, the electrical accelerometer signals 174*b* are communicated to stereo audio interface circuit 184 which may further condition the signals, for example to boost or shift low frequencies, or to multiplex more than one biosensor signal onto a single conductor. The stereo audio interface circuit 184 connects the resultant one or two signals to output conductors 29*b*. The PPG and accelerometer signals are communicated to mating connectors: an audio connector shown as a 4-conductor male audio plug 40a, and a docking connector 40b (having stereo audio recording inputs). The mating connectors 40a and 40b are received by their electrical connector counterparts on the mobile 12, audio connector 28a and docking connector 28b. In an alternative embodiment, the docking connector's serial connectors are used to transmit serial data over conductors 29b.

Figure 8:
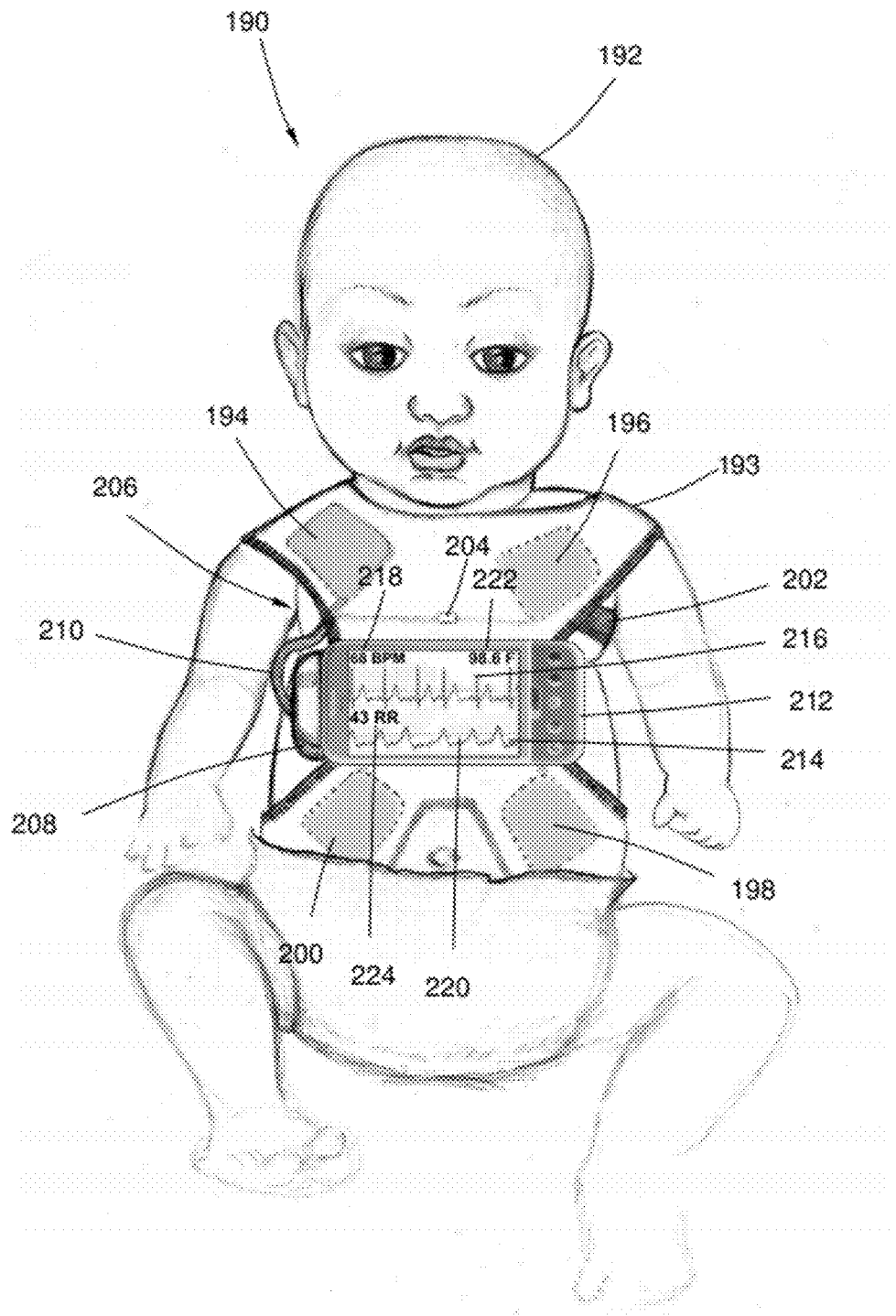
FIG. 8 is a top elevational view of another embodiment of the present invention having a ECG monitor, a respiratory monitor, and a body temperature sensor.

Referring now to FIG. 8, an embodiment of the biosensor interface apparatus 190 may be integrated into an emergency or pre-hospital critical care monitor having multiple biosensors. The biosensors are arranged so that the patient 192 may be wearing an ECG electrode retaining device such as garment 193 that holds cloth or textile ECG electrodes 192, 194, 196, 198 in communication with the patient's skin. There also may be an thermal sensor 202 for measuring the patient's body temperature (shown under the patient's arm), and a movement sensor accelerometer 204, which is in communication with the patient's thorax 206 measuring thoracic movement as a respiratory monitor. The interface device 208 receives the biosensor signals via electrical cable 210, processes the signals, and outputs them to the mobile communication device 212 via one or more electrical connectors. Various sensor signals and measurements may be displayed on the mobile's screen 214 such as electrocardiogram (ECG) 216, heart rate (BPM) 218, respiratory movement 220, respiratory rate (RR) 224, and body temperature (degrees Fahrenheit or Centigrade) 222. In another embodiment the connection of cable 210 to interface device 208 may have releasable connectors either for a single electrical cable such as 210, or as individual sensor connectors. In another embodiment one or more sensors communicate with the interface device 208 wirelessly such as with bluetooth-capable sensors. In another alternative embodiment, the patient is using adhesive ECG electrodes, and there is no retaining garment 193. In yet another embodiment the accelerometer 204 can be used to determine periods of activity, rest, and cessation of patient movement, as well as patient position. The movement sensor 204 can also track user 192 position, velocity and acceleration, either of a patient or a fitness user.

Figure 9:
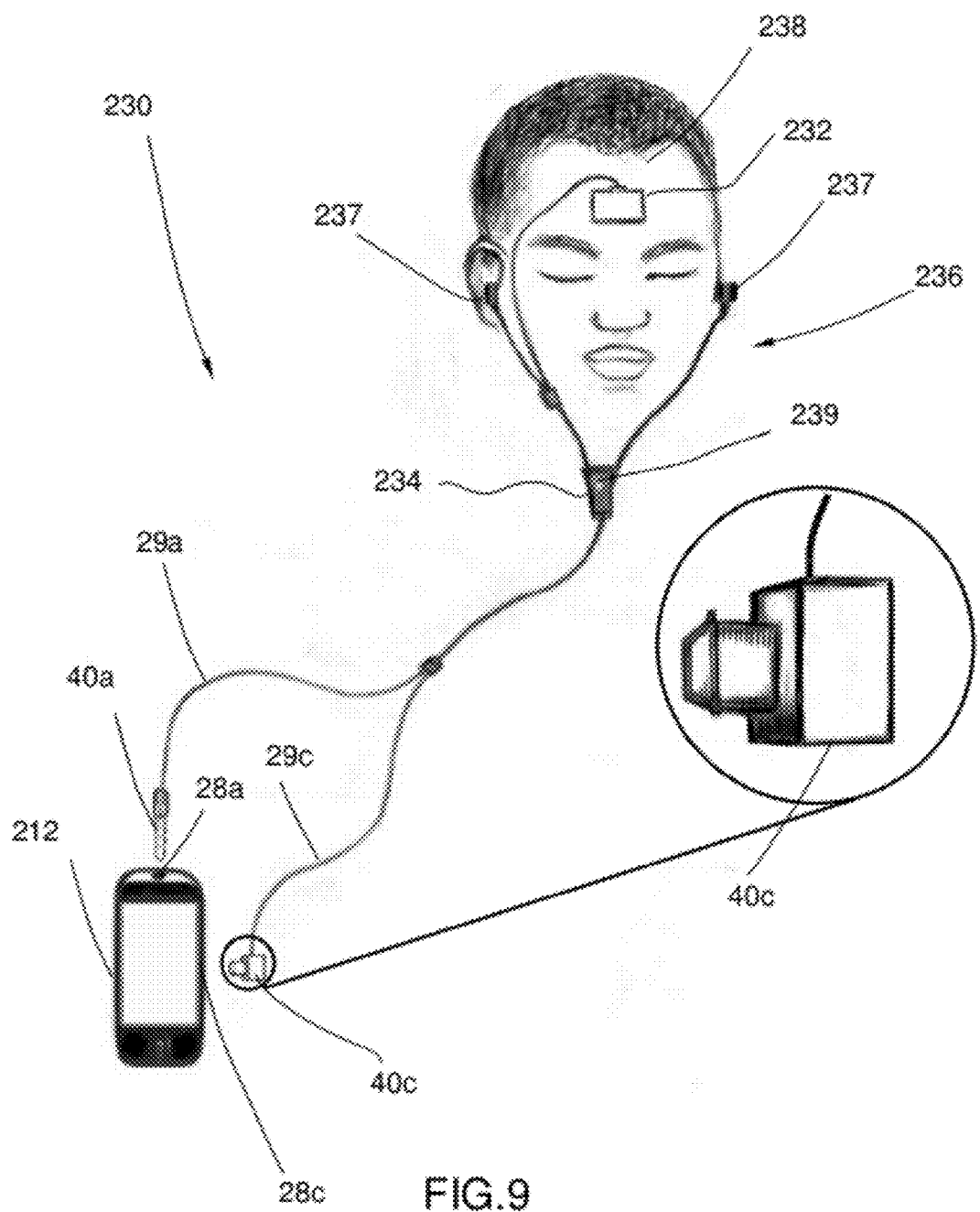
FIG. 9 is a top elevational view of an embodiment of the biosensor interface apparatus of the present invention with a close-up inset view of a connector.

Referring now to FIG. 9, an embodiment of the biosensor interface apparatus 230 may be integrated into headset 236 having multiple biosensors. The sensors assembly 232 adheres or is held in communication with the patient's forehead 238 and is in communication with interface device 234. The interface device 234 connects to mobile 212 via conductors 29a, 29c which terminate in male audio connector 40a and USB connector 40c. The audio connector 40a and USB connector 40c are received by the mobile's electrical connectors 28a and 28c respectively. The sensors assembly 232 may have a photo plethysmograph for determining the heart's BPM and a temperature sensor for detecting the patient's body temperature. The interface device 236 may provide audio signals to headset loudspeakers 237 and may have an integrated microphone 239. In addition the interface device 234 may also have an accelerometer so a prone patient having the interface device in communication with their chest to serve as a respiration sensor for determining respiratory rate (RR).

Figure 10:
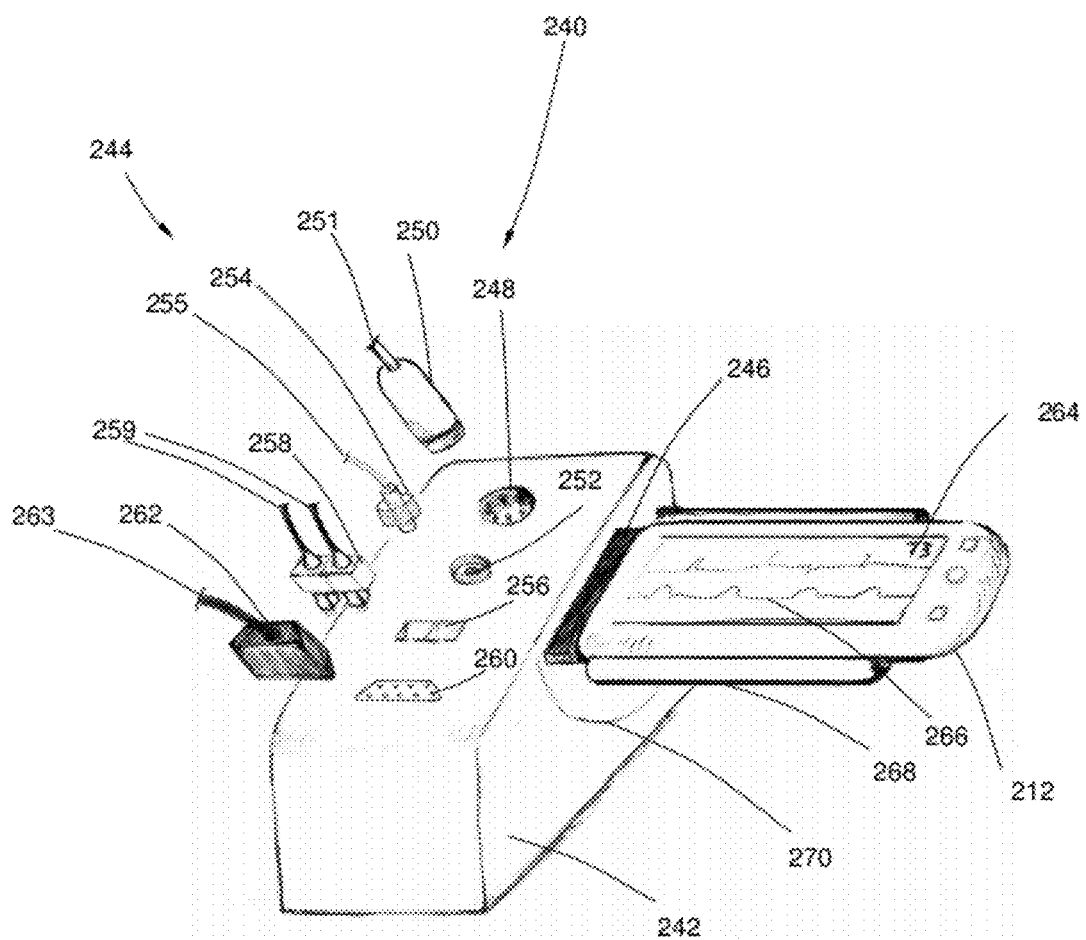
FIG. 10 is a front elevational view of another embodiment of the present invention having a dock receiving a variety of biosensor connectors and a smart phone.

Turning now to FIG. 10, an embodiment of the interface apparatus 240 may provide an interface device such as dock 242 in order to interface multiple medical or other biosensors 244 to mobile device 212. For example, dock 246 may provide a connector 248 to mate with the circular push-pull connector 250, which connects to one or more electrical signals 251 such as an ECG, EEG, or the like. The dock 246 may also provide a connector 252 to mate with an air tube connector 254, which provides air or other gas from a biosensor such as human breath 255 for a capnograph to measure $CO_2$. The dock 246 may also provide a connector 256 to mate with a fiber optic connector 258, which may provide one or more light signals 259 such as from a photo plethysmograph to measure BPM and the like. The dock 242 may have any number of other connectors for connecting biosensors and their associated leads and cabling including, for example, an electrical sub-d connector 260 to mate with connector 262, which may have one or more electrical biosensor signals 263 such as from an ECG or PPG. Other electrical connectors, optical connectors, and air/gas connectors configured to provide a biosensor signal are within the scope of the invention.

The biosensor signals 244 are received by mobile 212 through dock connector 246 which is in communication with an electrical connector on mobile 212 (not visible). The signals may be processed by the interface device dock 242 before being communicated to mobile 212. The biosensor signals may be further processed by the mobile 212 to produce measurements such as BPM 264 or for plotting signals for medical diagnosis such as ECG 266 and respiratory end-tidal $CO_2$ ($ETCO_2$) 267. Biosensor signals may also be received by one or more RF receivers in the dock 246 (not shown) and communicated to the mobile 212 via wired electrical connector 246, for example, to allow the wireless sensor to utilize the features of the wired audio input's anti-alias filters and analog to digital converter as will be explained in detail below.

Continuing with FIG. 10, interface device dock 242 may also include a support 268 for retaining the mobile 212 in communication with connector 246. The support 268 may be engaged to move the mobile 212, for example, by rotating a housing element 270 to improve viewing position or some other factor.

Figure 11:
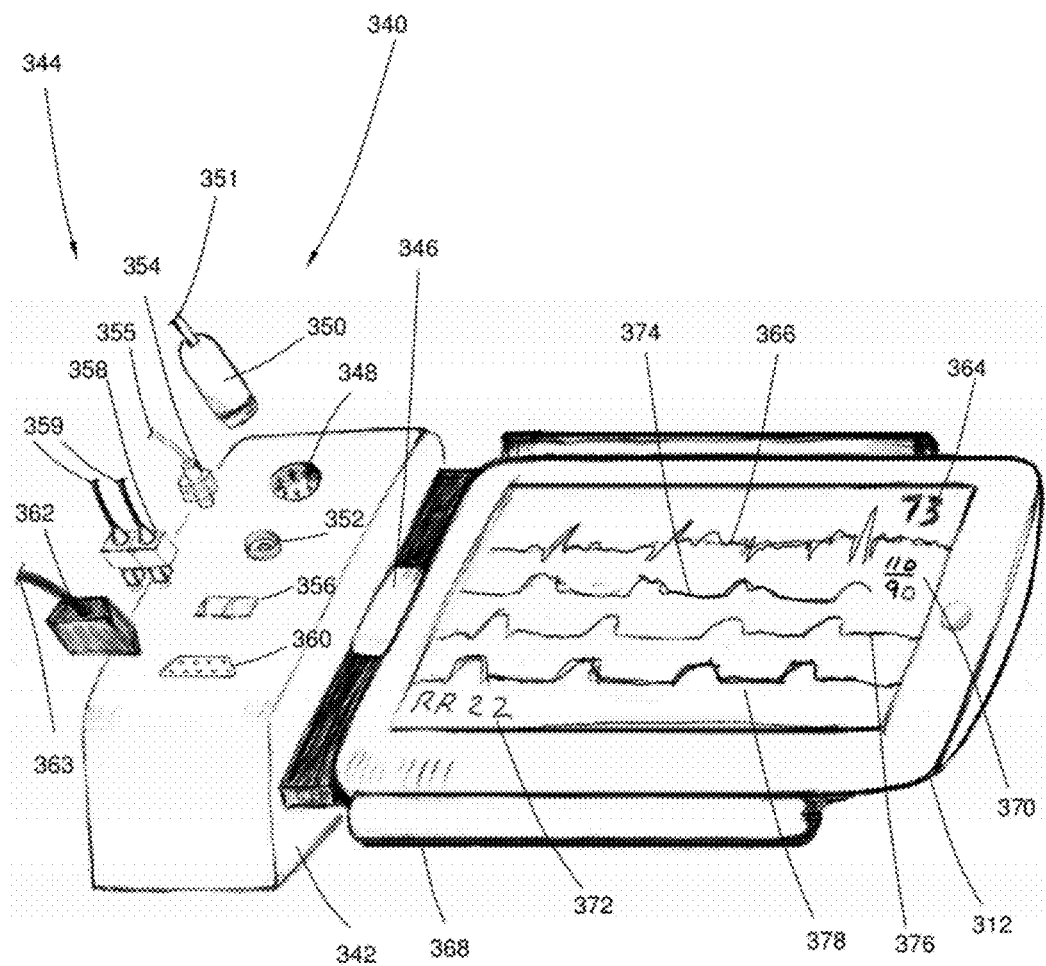
FIG. 11 is a front elevational view of another embodiment of the present invention having a dock receiving a variety of biosensor connectors and a tablet.

Referring now to FIG. 11, an embodiment of the interface apparatus 340 provides an interface device such as dock 342 that may connect multiple medical or other biosensors 344 to a mobile device such as tablet 312. For example, dock 342 may provide a connector 348 to mate with the circular push-pull connector 350, conducting one or more electrical signals 351 such as an ECG, EEG, trans-thoracic impedance (THO) or the like. The dock 342 may also provide a connector 352 to mate with a tube connector 354, which provides air or other gas from a biosensor such as human breath 355 for a capnograph to measure end-tidal carbon dioxide concentration ($ETCO_2$), respiratory nose/mouth flow (FLOW), airway respiratory rate (AWRR), and so forth. The dock 346 may also provide a connector 356 to mate with a fiber optic connector 358, which may provide one or more light signals 359 such as from a photo plethysmograph to measure BPM and the like. The dock 342 may have any number of other connectors for connecting biosensors and their associated leads and cabling including, for example, an electrical sub-d connector 360 to mate with connector 362, which may have one or more electrical biosensor signals 363 such as from an ECG or PPG. Additionally, other electrical connectors, optical connectors, and air/gas tube connectors configured to provide a biosensor signal are within the scope of the invention.

The biosensor signals 344 are received by a mobile device such as a tablet 312 through dock connector 346 which is in communication with an electrical connector on tablet 312 (not visible). The signals may be processed by the interface device dock 342 before being communicated to tablet 312. The biosensor signals may be further processed by the tablet 312 to produce displayed measurements such as BPM 364, diastolic and systolic blood pressure 370, respiratory rate 372, and the like. As well, the biosensor signals may be plotted or otherwise displayed, either with further processing by tablet 312, or plotted in the form received from dock 342. For example, biosensor signals may be displayed by tablet 312 such as those used for medical diagnosis and monitoring: ECG 366, PPG cardiac signal 374, respiratory motion 376, end-tidal $CO_2$ ($ETCO_2$) 378, and the like. Biosensor signals may also be received by one or more RF receivers in the dock 346 (not shown) and communicated to the tablet 312 via wired electrical connector 346, for example, to allow the wireless sensor to utilize the features of the wired audio input's anti-alias filters and analog to digital converter. Interface device dock 342 may also include a support 368 for retaining the mobile 312 in communication with connector 346.

Figure 12:
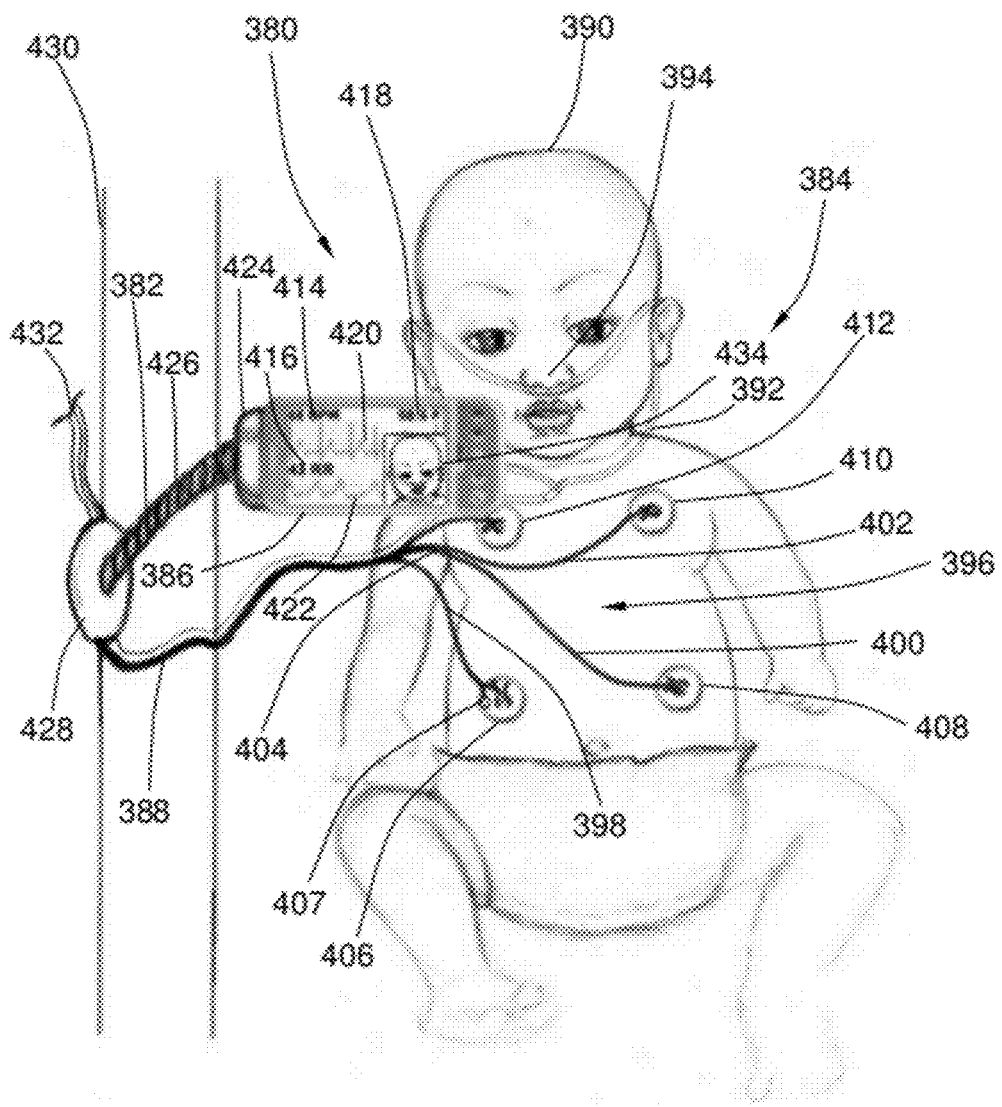
FIG. 12 is top elevational view of another embodiment having a capnograph, an ECG, a respiratory sensor, and a temperature sensor.

Referring now to FIG. 12, an embodiment of the interface apparatus 380 provides an interface device such as dock 382 that may connect multiple medical or other biosensors 384 to a mobile device such as smart phone 386. For example, the dock 384 may also provide an air tube such as capnograph sampling tube 388, which provides exhaled breath from a patient 390. For example, the capnograph sampling tube 388 may be in communication with a split cannula 392 such that human breath escaping from nose 394 is conducted by sampling tube 388 to interface device 382 having a device to measure carbon dioxide ($CO_2$) and airflow. The dock 384 may also have integrated or connected ECG leads 396, for example, having 4 conductors 398, 400, 402, 404 connected to ECG electrode pads 406, 408, 410, 412 in electrical communication with human 390, for example with adhesive or suction. In addition, there may also be an electrical motion sensor signal 407 for measuring respiratory rate, and a temperature sensor, for example, in communication with the patient's skin via an ECG electrode pad such as 406 (not visible).

Continuing with FIG. 12, the biosensor signals are received by a smart phone 386 through dock connector 382, which is in communication with an electrical connector on smart phone 386 (obscured). The interface device dock 382 converts the human breath and human biopotential signals from sampling tube 388 and ECG leads 396 respectively into electrical signals suitable for communication to the smart phone 386 via one or more of the smart phone's electrical connectors such as a USB connector, a docking connector, or a headset connector. The electrical biosensor signals may be further processed by the smart phone 386 to produce displayed measurements such as BPM 414, respiratory rate 372, body temperature 418, and the like. As well, the biosensor signals may be plotted or otherwise displayed. For example, biosensor signals may be displayed by smart phone 386 such as ECG 420, $ETCO_2$ 422, and the like. Biosensor signals may also be received by one or more RF receivers in the dock 346 (not shown) and communicated to the smart phone 386 via wired electrical connectors. Interface device dock 382 may also include a connecting and supporting component 424 for communicating with electrical connectors and retaining the smart phone 386. The connecting and supporting component 424 may have an attached neck or supporting component 426, which may be connected to base 428. The neck 426 may be articulated or otherwise provide a position for smart phone 386 such that the patient 390 is viewable for video monitoring or audible for audio monitoring 434. Base 428 may provide a secure mechanism for attaching the interface apparatus 380 to, for example, an incubator side 430. In addition, interface apparatus 380 may have an external source of AC or DC electrical power 432, which may provide electrical power to smart phone 386 through the electrical connectors in communication with connecting and supporting component 424. Further, all signals received by the smart phone 386, such as ECG, ETCO2, body temperature, respiratory movement, video, and audio may be transmitted wirelessly by smart phone 386 or via a cable connected to the mobile for remote monitoring and storage.

Figure 13:
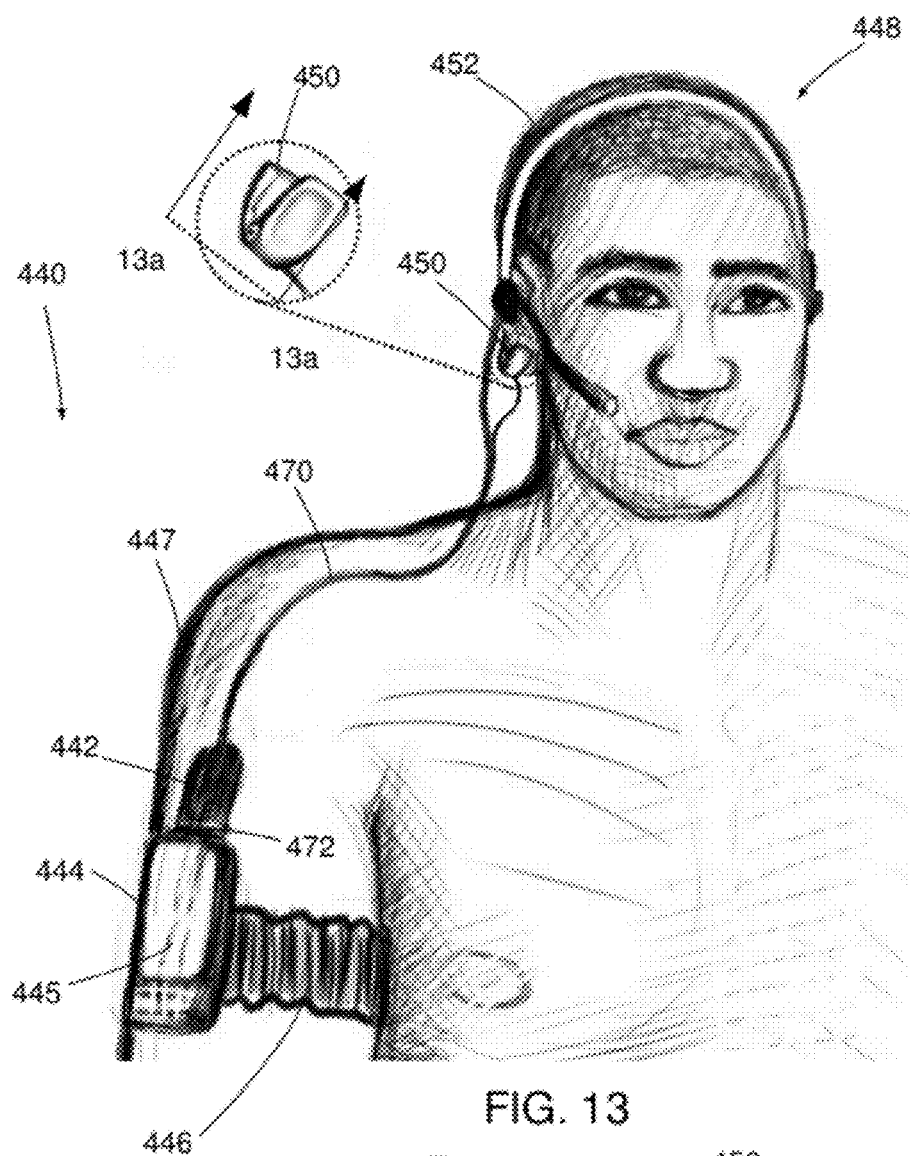
FIG. 13 is front elevational view of another embodiment having a PPG worn on an earlobe and a sphygmomanometer worn on the upper arm with an inset close up of the PPG.

Turning now to FIG. 13, an embodiment of the interface apparatus 440 comprises an interface device 442 that may connect multiple medical or other biosensors to a mobile device such as smart phone 444 via electrical connector, for example 472. The biosensors may include a sphygmomanometer such as inflatable blood pressure cuff 446 to measure or monitor the user's blood pressure. The blood pressure cuff 446 may be in communication with the user's arm 447 and may also house or otherwise carry mobile 444. The embodiment of interface apparatus 440 may also have an integral headset 448 worn by user 452, and a PPG 450, for example, attached to the user's earlobe. Mobile device smart phone 444 may derive measurements and display plots of the biosensor data on its display 445. Smart phone 444 may also transmit the patient's biosensor data and measurements using one or more internal RF transmitters, for example, over the mobile's data network, or as as modulated data, using frequency shift key (FSK), phase shift key (PSK) encoding or like modulation schemes over the mobile's voice network. In addition, the mobile 444 may transmit the data over a serial cable or an RF bluetooth channel, to a PC or other computing device, or via various other such wireless and wired interfaces, such as 3G, 4G, wired and wireless Ethernet and the like.

Figure 13A:
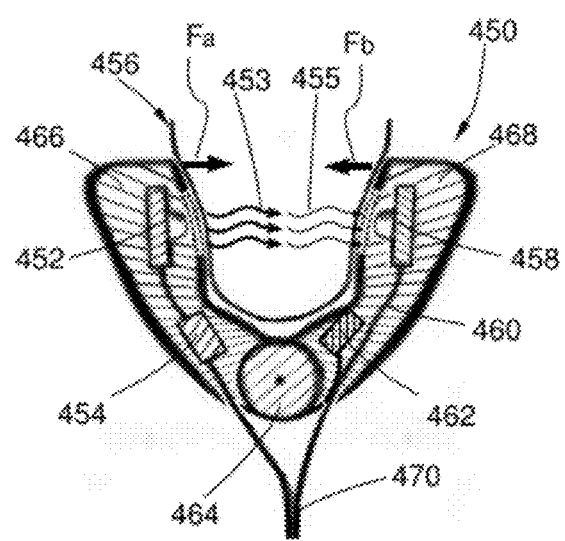
FIG. 13a is cross-section view of the PPG of FIG. 13 taken along the 13a axes.

Turning now to FIG. 13a, a cross section of photo plethysmograph 450 taken along axes 13a is shown. The PPG 450 contains a light emitting element such as IR LED 452. The LED 452 emits a light 453 when activated by power from a power control unit 454. The light 453 has a substantially distinct wavelength such as 880 nanometers or 920 nanometers. The light 453 enters the human tissue having a blood flow such as in earlobe 456. The light is partially absorbed, or otherwise filtered by the blood flowing in the earlobe 456 and emerges as light signal 455, carrying a blood flow signal. The light signal 455 is received by the light signal receiving device 458, which transforms the energy from the photons of the light signal 455 into a corresponding electrical signal. In one embodiment the light receiving device 458 is a photo diode, in another embodiment the receiving device 458 is a photo transistor, in yet another embodiment the light receiving device 458 has an internal amplifier for amplifying the output signal, for example, transmitted over conductor 460.

The PPG 450 may releaseably attach to the user's earlobe 456 by using a biasing element 464 that provides forces $F_a$ and $F_b$ which grip earlobe 456 between opposing elements 466, 468. Elements 466, 468 may also house IR LED 452, power control unit 454, light receiving device 458, motion/temperature sensor 462, and the like. Additionally, PPG 450 is connected via conductors 470 to interface device 442, which may transmit one or more sensor signals and power.

Turning now to FIG. 14, an embodiment of the interface apparatus 480 comprises an interface device 482 that may connect multiple medical or other biosensors to a mobile device such as smart phone 484 via an electrical connector in communication with interface device 482. The biosensors may include a sphygmomanometer such as inflatable blood pressure cuff 486 to monitor the user's blood pressure. The blood pressure cuff 486 may be in communication with the user's arm 487 and may also house or otherwise carry mobile 484. The embodiment of interface apparatus 480 may also have an integral headset 448 worn by user 489, and a PPG 490, for example, in communication with a user's forehead 485. Mobile device smart phone 444 may derive measurements, display plots, transmit medical records of biosensor data, and so forth.

Turning now to FIG. 15, a cross section of photo plethysmograph 490 taken along axes 15 is shown. Referring also to the PPG 490 shown in isometric view in FIGS. 14 and 16, the PPG 490 contains a light emitting element such IR LED 492. A light 493 is emitted from the LED 492 with a substantially distinct wavelength such as 880 nanometers or 920 nanometers. The light 493 enters the human tissue 496 having a blood flow such as forehead 485. The light is partially absorbed, or otherwise filtered by the blood flowing in the tissue 496, is reflected off bone 498, and emerges as light signal 495 carrying blood flow signal. The light signal 495 is received by the light signal receiving device 499, which transforms the energy from the photons of the light signal 455 into a corresponding electrical signal. Biosensors may also include a temperature sensor 497 to measure the user's body temperature in thermal communication with the user's skin 491. The PPG 450 and temperature sensor 497 may be contained in sensors housing 481 which can be brought into communication with the user's forehead 456 by using a mounting or retaining device such as hat 483 worn by user 489. Additionally, PPG 490 and thermal sensor 498 are connected via conductors 470 to interface device 482 which is mated to one or more electrical connectors on smart phone 484. Other embodiments may retain the sensors using a headband, a visor, a cap, other types of hats, adhesive bands, and so forth.

Figure 17:
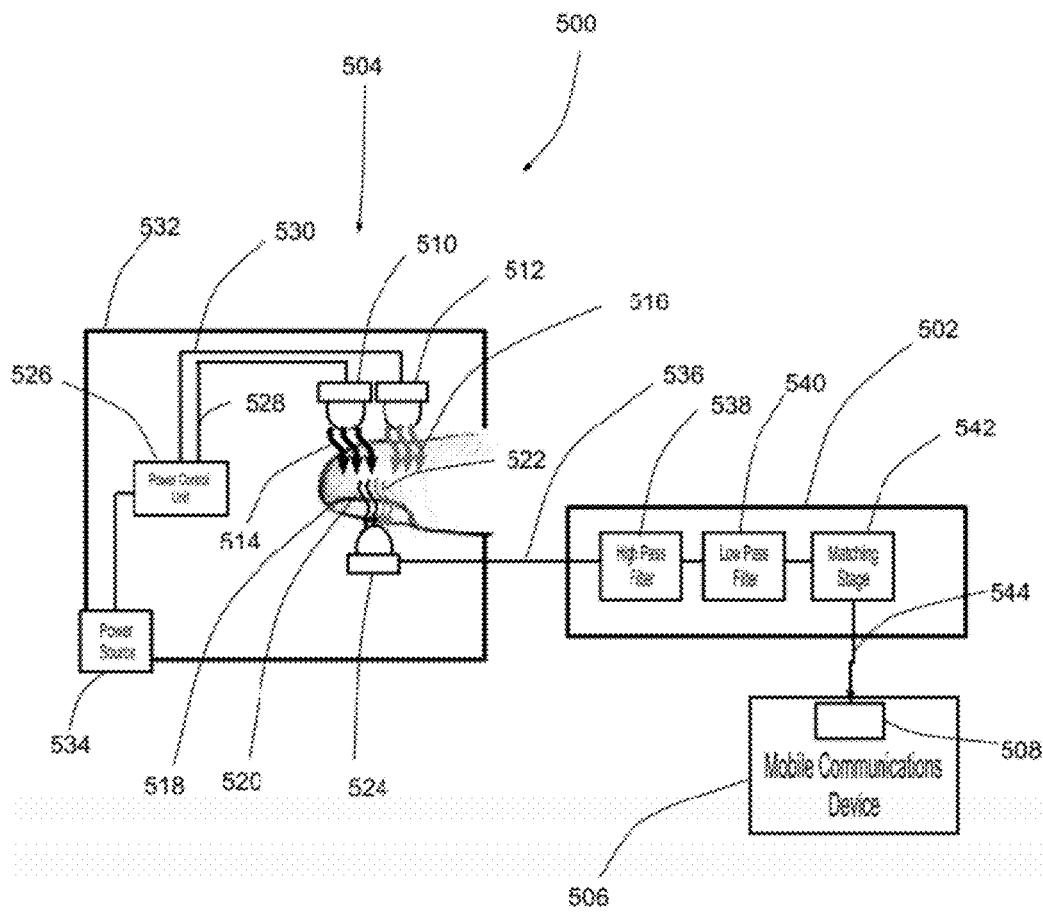
FIG. 17 is a block diagram of another embodiment of the present invention having a pulse oximeter.

Referring now to FIG. 17, a block diagram of an embodiment of the interface apparatus 500 comprises an interface device 502 that may connect multiple medical or other biosensors such as pulse oximeter 504 to a mobile device such as smart phone 506 via an electrical connector 508 in communication with interface device 502.

Continuing with FIG. 17, the pulse oximeter 504 has, for example, two LED light-emitting elements 510, 512 emitting two different frequencies of light, for example red light 514 with a wavelengths of substantially 660 nanometers, and infrared light 516 with wavelengths of substantially 940 nanometers. The light 514, 516 is partially transmitted through fingertip 518 and emerges as modulated light 520, 522 respectively, now having a cardiac signal and information about the saturated percentage of oxygen in the blood, referred to as $SPO_2$. The user's heart rate and other information may be derived from the pulse oximeter signal as well. The information containing light 520,522 strikes light receiving device such as photo transistor 524 which transforms the photonic energy to a corresponding electrical signal transmitted via one or more conductors 536 to interface device 502.

Figure 18:
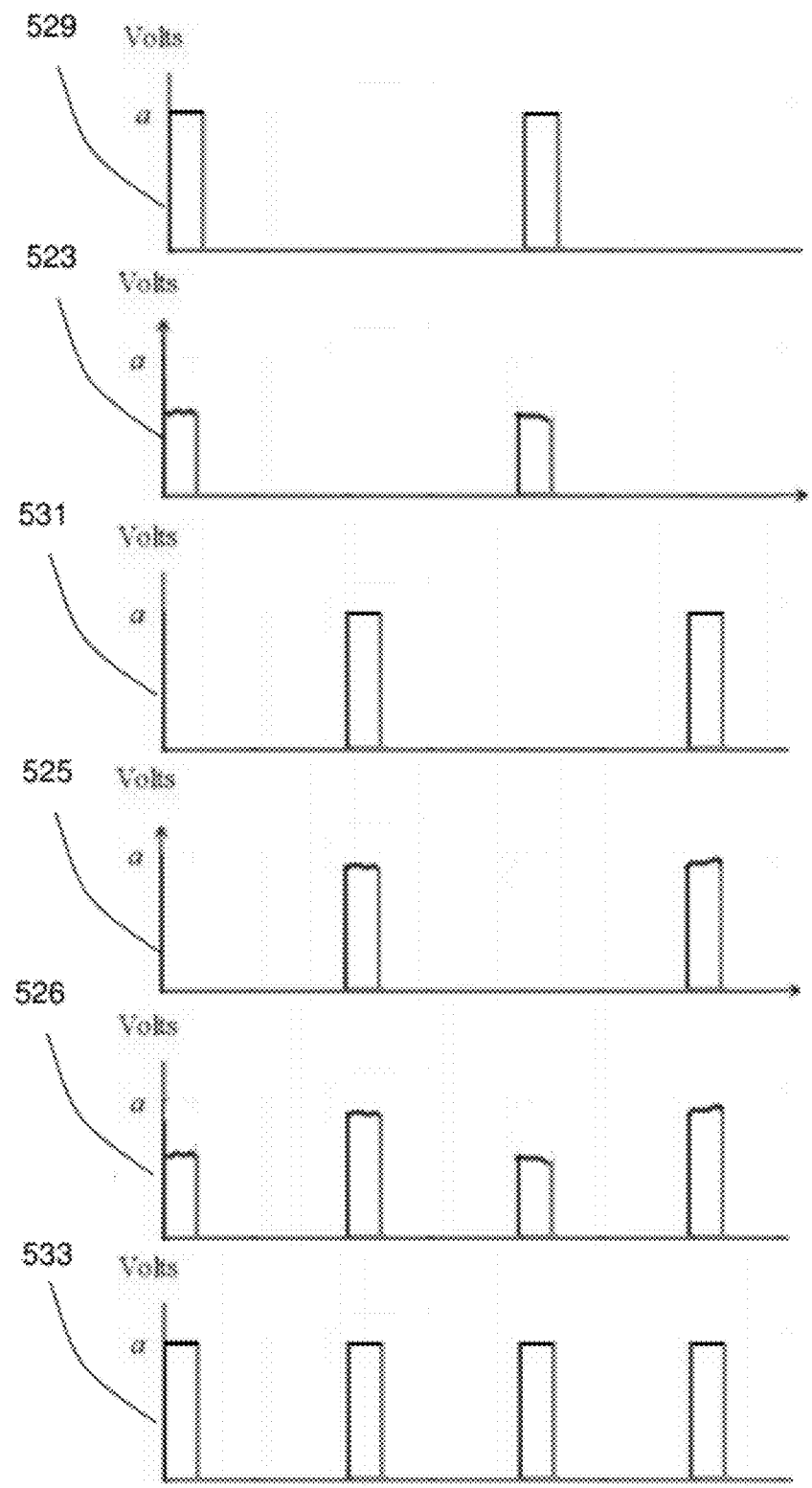
FIG. 18 is a sequence of signal plots showing time division multiplexing of pulse oximeter data.

Referring to FIGS. 17 and 18, to determine $SPO_2$ the LEDs 510, 512 may be turned on alternately and without overlapping with power control unit 526 and LED control lines 528, 530 as shown by voltage plots 529, 531 respectively. The information containing light 520, 522 has separate contributions shown in plots 523, 525. The alternating lights 520, 522 are received and combined (multiplexed) by a single receiver 524 as shown in plot 526. Further processing of the signal to yield $SPO_2$ must separate (demultiplex) the two signals into their individual components 523, 525. The signals 529, 531, and 533, or information derived therefrom may be supplied to the mobile device 506 to demultiplex the pulse oximeter data as well as other sensor data (see detailed description of FIG. 19 below).

Note that power source for the pulse oximeter may be an element of the sensors assembly 532 as shown. Alternatively, the power source may also be an element of the interface device 502 or the mobile communications device 506 which may supply power through a microphone bias supply or a DC voltage supply (not shown).

Still referring to FIGS. 17 and 18, the interface device 502 may receive pulse oximeter and other sensors signals on conductors 536 and perform various transformations on the signals. For example, high frequency noise may be reduced with high pass filter 538, DC offsets and baseline wander can may be reduced with a low pass filter 440, These filters may be instrumental in creating a signal which is usable for examples as a diagnostic display, an $SPO_2$ calculation, a BPM calculation, and so forth. Internal mobile device filters, for example such as an anti-aliasing filter for recording inputs or a CODEC filter may be used. Alternatively, internal filters can be reconfigured or disabled to allow, for example, the reception of lower frequency signals by the mobile 12 CODEC 76 or AtoD converter 78.

In addition, proper matching of the electrical characteristics of mobile's electrical connector may provided by matching stage 542 so that connecting of mating connector 544 to the mobile's electrical connector 508. This may involve matching impedance for detection of the device by the smart phone. It may also involve attenuation or amplification of the input signal to match the dynamic range of the mobile's microphone or recording inputs.

Figure 19:
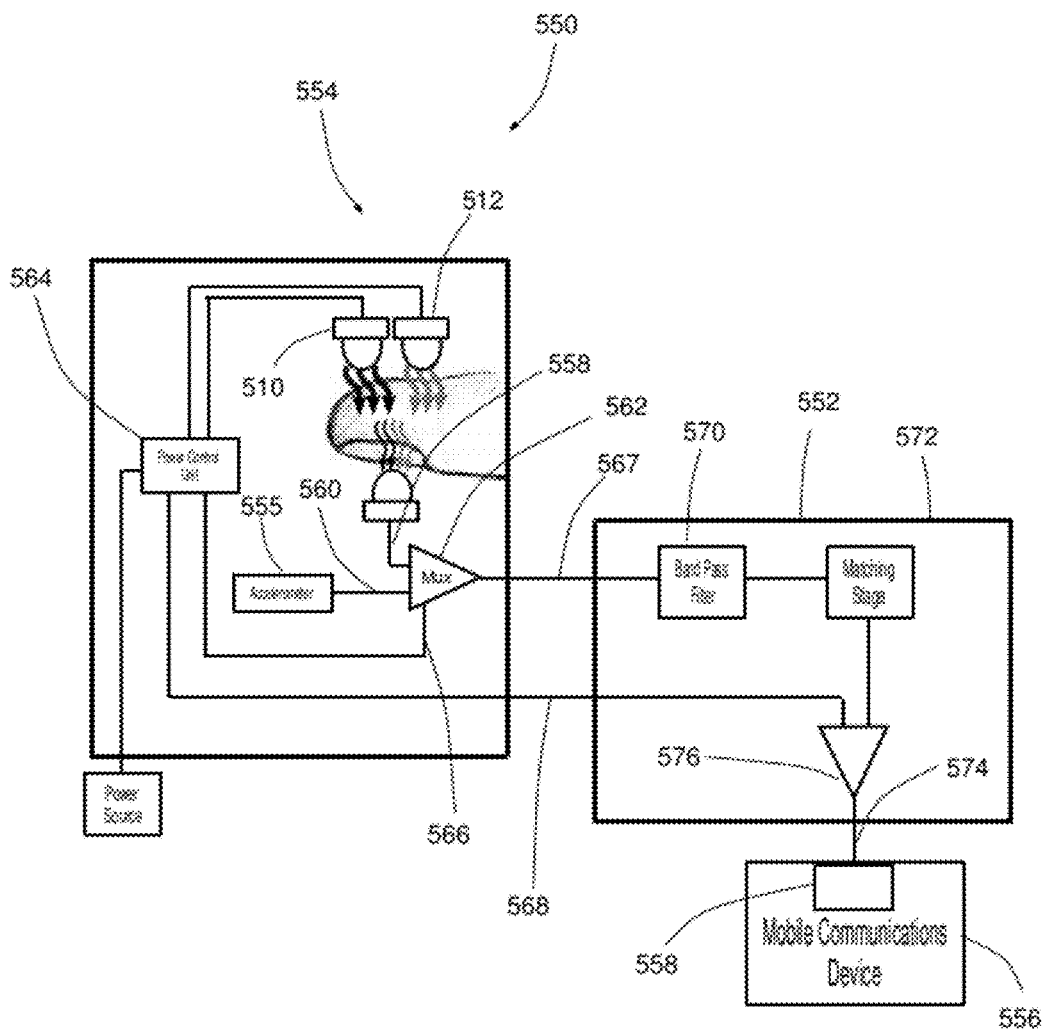
FIG. 19 is a block diagram of another embodiment having a multiplexer combining a pulse oximeter and an accelerometer motion sensor.

Turning now to FIG. 19, but also referring to FIG. 18, a block diagram of an embodiment of the interface apparatus 550 comprises an interface device 552 that may connect multiple medical or other biosensors such as pulse oximeter 554 and motion sensor accelerometer 555 to a mobile device such as smart phone 566 via an electrical connector 558 in communication with interface device 552.

The pulse oximeter output signal 558 may be multiplexed with accelerometer signal 560 by multiplexer 562. Recall that the LEDs 510, 512 may be turned on alternately and without overlapping with power control unit 526. Similarly, power control unit 564 may supply a signal to the multiplexor 562 to time multiplex the accelerometer and pulse oximeter signals 566 into a combined signal 567. Further processing of the signal to yield $SPO_2$ must separate (demultiplex) the two signals combined in pulse ox output 558 and the accelerometer output 569 into their three individual components (and perhaps more for additional accelerometer outputs). The power control unit 564 may provide a synchronizing signal such as 568 to the mobile device 556 to demultiplex the pulse oximeter data and accelerometer data. The synchronizing signal 568 may be further combined with the sensor data by another multiplexer 576.

Still referring to FIG. 19, the interface device 552 may receive pulse oximeter, other sensors signals, and synchronizing signals on conductors 567, 568 and perform various transformations on the signals. For example, high frequency noise, DC offsets and baseline wander may be reduced with a band pass filter 570. In addition, proper matching of the electrical characteristics of mobile's electrical connector may provided by matching stage 572, for example, as provided by matching stage 542 above.

Figure 20:
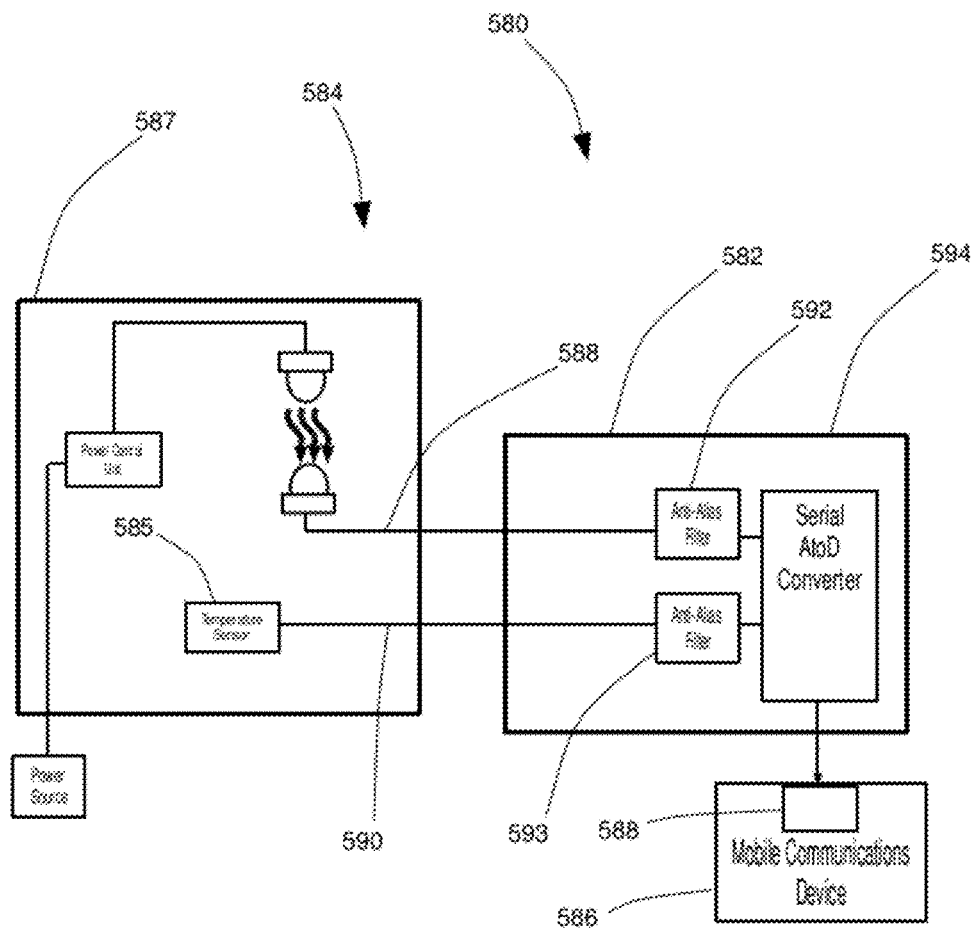
FIG. 20 is a block diagram of another embodiment having a PPG and a temperature sensor with analog to digital conversion and serialization.

Referring next to FIG. 20, a block diagram of an embodiment of the interface apparatus 580 comprises an interface device 582 that may connect multiple medical or other biosensors such as photo plethysmograph 584 and temperature sensor 585 to a mobile communications device 586 via an electrical connector 588 in communication with interface device 582.

The photo plethysmograph output signal and temperature sensor signal may be communicated from sensors assembly 587 by separate (i.e. parallel) conductors 588, 590 to interface device 582. High frequency noise, DC offsets and baseline wander may be reduced with anti-alias filters 592, 593. The filtered signals are received by the serial AtoD converter 594, which converts them to digital values that are serialized for transmission to serial electrical connector 588 on mobile 586.

Figure 21:
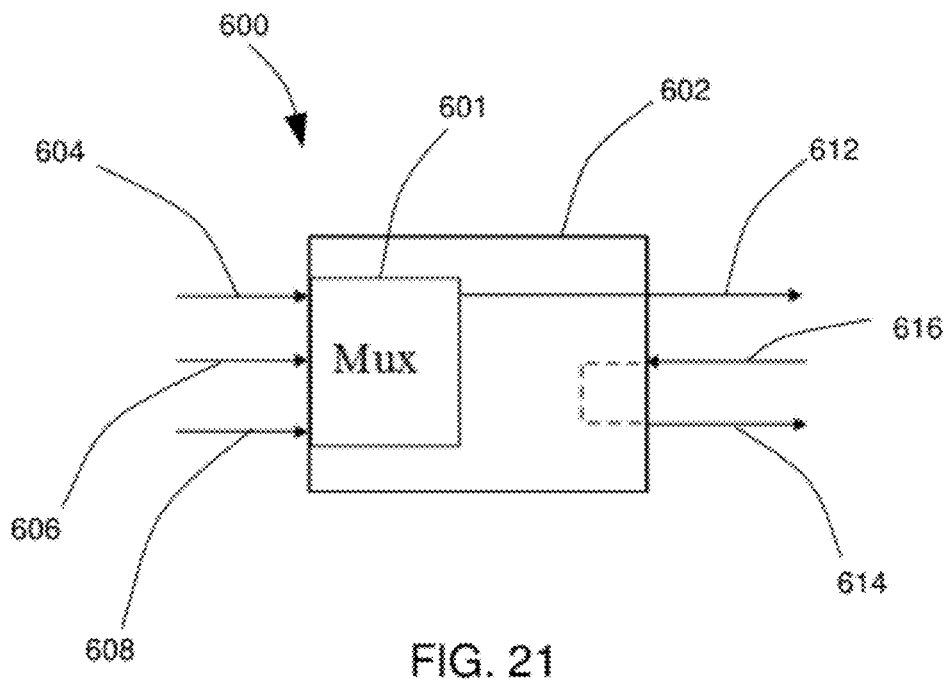
FIG. 21 is a block diagram of another embodiment of the biosensor interface apparatus including a multiplexer receiving a microphone input along with biosensor inputs.
Figure 22:
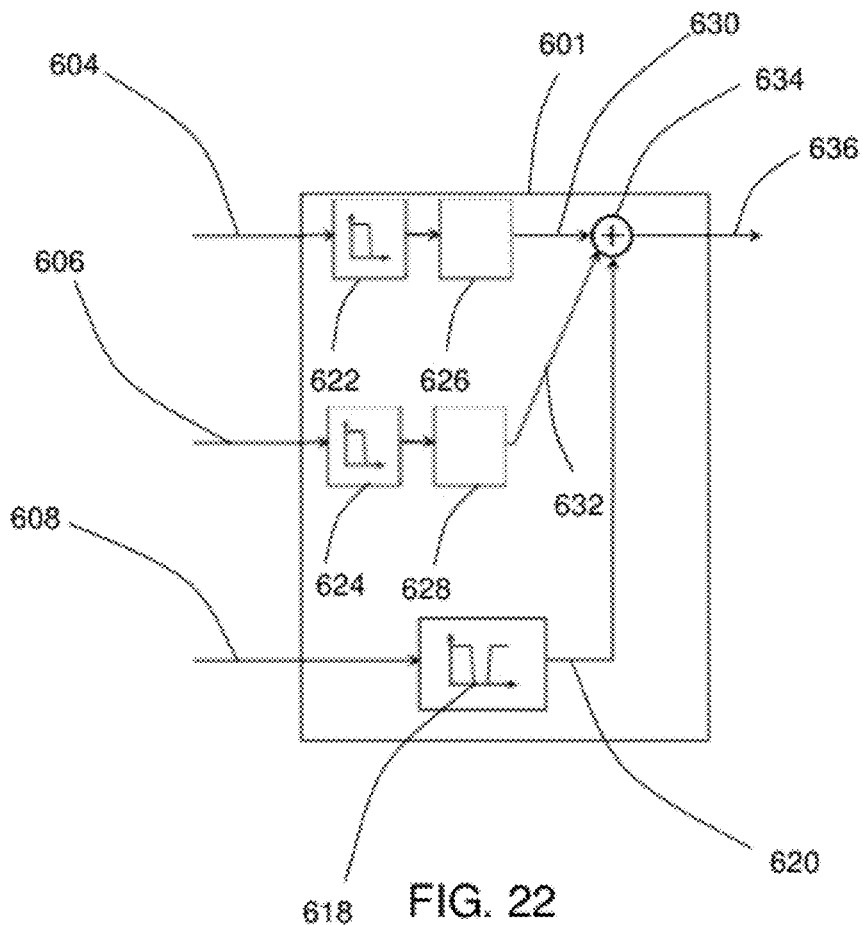
FIG. 22 is a block diagram of the frequency division multiplexer of FIG. 21.
Figure 23:
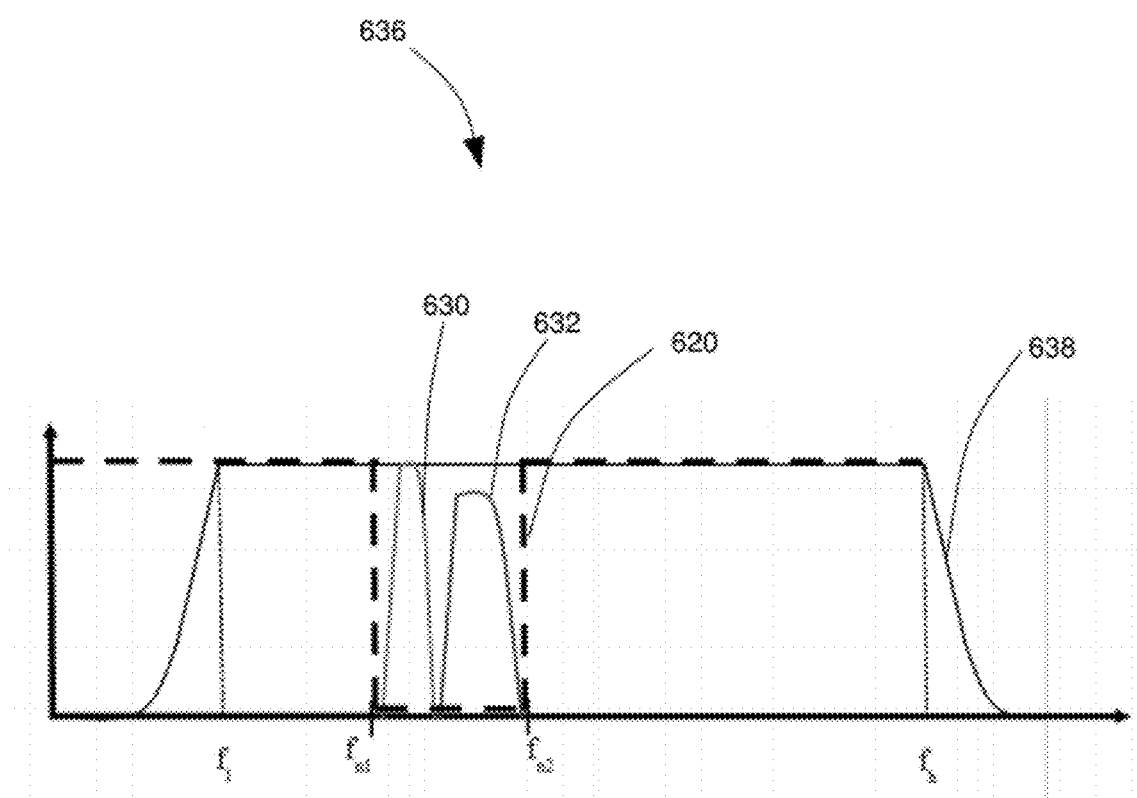
FIG. 23 comprises frequency plots demonstrating the frequency division multiplexing of the multiplexer of FIGS. 21 and 22.

Referring now to FIGS. 21-23, an embodiment of the interface apparatus 600 may comprise an interface device 602 that has a frequency multiplexer 601. The interface device may connect multiple signals such as pulse oximeter signal 604, body temperature signal 606, microphone signal 608, which are combined by multiplexer 601 into a signal that may be transmitted to one or more mobile electrical audio inputs 612. The interface device 602 may also provide outputs for a headsets loudspeakers 614 allowing the headset to connect to the audio connector loudspeaker outputs 616, that may otherwise be utilized by interface device 602. Similarly, the interface device 602 microphone input 608, that may otherwise be utilized by interface device 602. The frequency multiplexer 601 may combine the signals 604, 606, 608 in a number of ways. For example, the microphone input 608 may be transformed by notch filter 618 to remove a portion of the signal between frequencies $f_{n1}$ and $f_{n2}$ as shown by frequency profile of notch filter output signal 620. The sensor inputs 604, 606 may be transformed by low pass filters 622, 624 and frequency shifted by modulators 626, 628 such that they are non-overlapping and within the notch 620 of notch filter 618 as shown by frequency plots of signals 630, 632. The filtered microphone signal 620 and the filtered and shifted sensors 630, 632 are combined by summer 634 to form the combination signal 636 which is received by a mobile device's audio input having bandwidth from $f_l$ to $f_h$ 638. Alternatively, the data may be modulated and/or multiplexed by any number of modulation schemes such as frequency shift key (FSK), phase shift key (PSK) encoding or the like.

The biosensor signals 630, 632 are recoverable by demultiplexing the information from the combined signal 636 by applying, for example, band pass filters and performing frequency shifting/demodulation. The microphone signal is restored by notch filtering out the signals between $f_{n1}$ and $f_{n2}$. These transformation may be performed on digital data sampled from the audio inputs.

Figure 24:
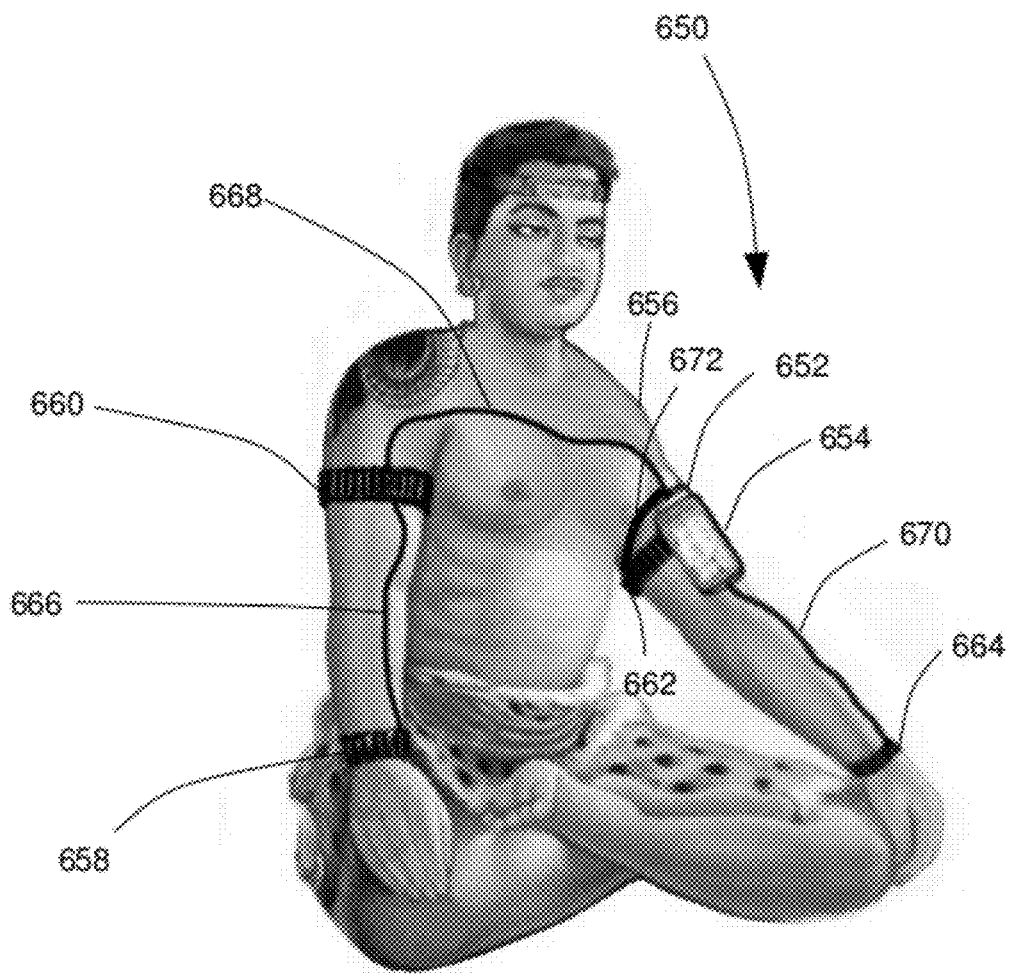
FIG. 24 is front elevational view of another embodiment having a ECG with fabric electrodes worn in cuffs on the upper and/or lower arms.

Referring now to FIG. 24, an embodiment of the interface apparatus 650 may comprise an interface device 652 connected to smart phone 654 being worn on a user's arm 656. The embodiment comprises an ECG having ECG electrodes in communication with the user's skin, such as cuffs having fabric electrodes 658, 660, 662, 664. The electrical signals received by the cuffs 658, 660, 662, 664 are communicated to the interface device 652 via ECG leads 666, 668, 670, 672, which transmits the signal's data to the mobile 654 via an electrical connector. Other embodiments may have more or less electrodes in differing arrangements. For example one embodiment may have as few as two electrodes, which may be a pair of upper arm cuffs 660, 662; or a pair of lower arm electrodes 658, 664. As well, the ECG electrodes need not be fabric, but can be standard adhesive electrodes, suction cup electrodes, and the like.

Figure 25:
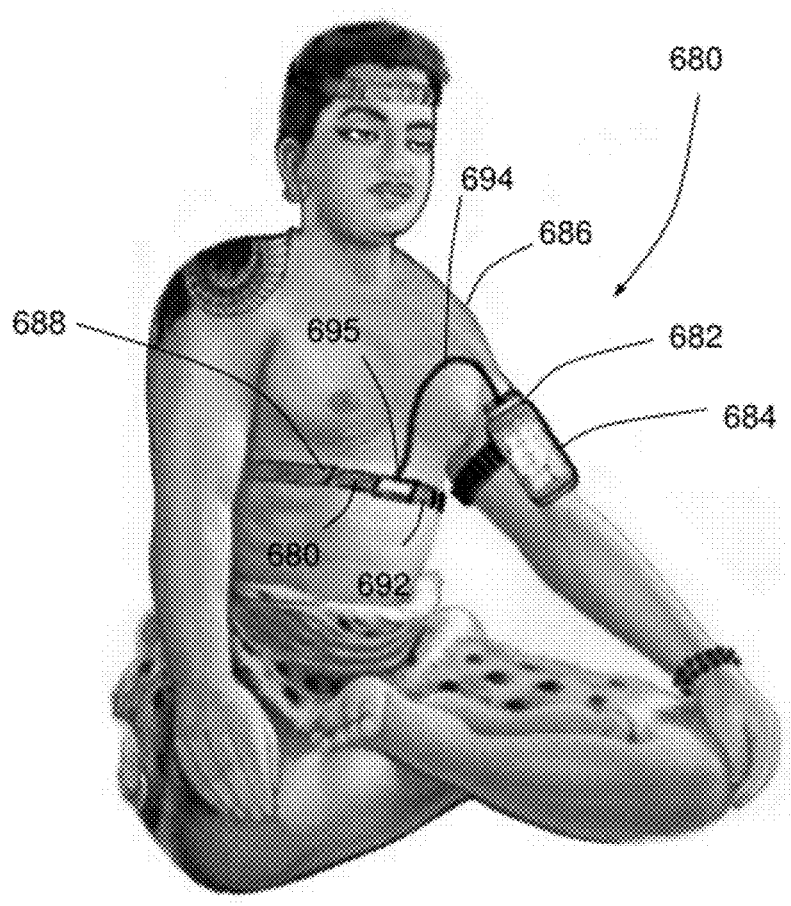
FIG. 25 is front elevational view of another embodiment having an ECG with fabric electrodes worn in strap across the torso.

Turning now to FIG. 25, an embodiment of the interface apparatus 680 may comprise an interface device 682 connected to media player 684 being worn on a user's arm 686. The embodiment 680 comprises an ECG having ECG electrodes in communication with the user's skin, such as ECG torso strap 688 having fabric electrodes 690, 692. The electrical signals received by the cuffs 690, 692 are communicated to the interface device 682 via electrical cable 684, which transmits the signal's data to the mobile 658 via an electrical connector. Other embodiments may have more or less electrodes in differing arrangements. As well, the ECG electrodes need not be fabric, but can be standard adhesive electrodes, suction cup electrodes, and the like. The ECG strap 688 may also have a central element 695 that connects to the ECG electrodes, for example, with a TBD snaps, stays, In one aspect of another embodiment (not shown), the biosensor interface apparatus further includes at least on least one receiver capable of receiving a wireless biosensor signal. The interface apparatus acts as an adapter for the wireless biosensor to utilize the capabilities of the mobile's electrical connectors. Importantly, wireless RF biosensors may need access to the mobile via its electrical connector, for example, with an iPhone® to avoid licensing issues.

It is noted that many changes and modifications may be made to the present invention without departing from the spirit thereof. The scope of some of these changes is discussed above. The scope of others will become apparent from the appended claims.

We claim:

1. A bio sensor interface apparatus comprising: a cell phone adapted to provide electrical data communication to a second device for communication to remote medical personnel, the cell phone having at least one electrical connector thereon, the electrical connector having a plurality of conductors wherein one or more of the conductors is an input conductor in communication with a mobile communications device processor of the cell phone, the cell phone including a graphical display adapted to display a plotted biosensor signal; an interface device in communication with at least two ECG biosensor signals, the interface device having one or more mating connectors configured to be mechanically received by the at least one electrical connector on the cell phone, wherein the interface device includes a multiplexer transforming the at least two ECG biosensor signals to a compatible electrical signal that is receivable by one or more input conductors of the electrical connector of the cell phone by multiplexing the at least two ECG signal together; and wherein the cell phone operates to display simultaneous the at least two ECG biosensor signals on the display and to transmit at least two ECG biosensor signals to the second device; a power source in at least one of the cell phone and the interface device for powering the interface device.

2. The bio sensor interface apparatus of claim 1 wherein the cell phone is a smartphone.

3. The bio sensor interface apparatus of claim 1 wherein the electrical connector is an audio connector configured to receive an electrical audio signal.

4. The bio sensor interface apparatus of claim 3 wherein the audio connector has one or more input conductors selected from a group consisting of microphone level input conductors, and audio recording line level input conductors.

5. The bio sensor interface apparatus of claim 3 wherein the mating connector is one or more analog audio connectors selected from a group consisting of a male 2.5 mm 3-conductor plug, a male 2.5 mm 4-conductor plug, a male 3.5 mm 3-conductor plug, a male 3.5 mm 4-conductor, a manufacturer specified stereo recording input plug or plugs, a manufacturer specified headset connector, and a manufacturer specified microphone connector.

6. The bio sensor interface apparatus of claim 1 wherein the electrical connector is a hybrid connector configured to receive serial data and to receive at least one electrical audio signal.

7. The bio sensor interface apparatus of claim 1 wherein the electrical connector is a serial connector configured to receive serial data.

8. The bio sensor interface apparatus of claim 7 wherein the interface device mating connector is one or more selected from a group consisting of a USB Mini-A, USB Mini-B, USB Micro-AB, USB Micro-B, USB Type A, USB Type B, and a 4-pin electrically compatible USB connector having a non-standard connector or housing.

9. The bio sensor interface apparatus of claim 1 wherein the electrical connector is one or more selected from a group consisting of an audio connector configured to receive an electrical audio signal, the serial connector configured to receive serial data, and the hybrid connector configured to receive serial data and to receive at least one electrical audio signal.

10. The bio sensor interface apparatus of claim 9 wherein the interface device mating connector is selected from a group consisting of an Apple® iPod® media player and iPhone® 30 pin connector; an Audiovox® cell phone 22 24, or 26 pin connector; an Ericsson® cell phone 10 pin connector; a Kyocera® cell phone and MP3 player 16 pin connector; a Motorola® cell phone 4, 5, 15, 17, and 26 pin connector: a Nokia® cell phone 14 pin connector; a Qualcomm® cell phone 15 pin connector; a Samsung® Cell Phone and PDA 5 or 19 pin connector; a Sanyo® cell phone 16 or 18 pin connector; a Siemens® cell phone 12 pin connector; a 4-pin electrically compatible USB connector; and a manufacturer specified docking connector.

11. The bio sensor interface apparatus of claim 1 wherein the interface device also transforms the at least two ECG biosensor signals to a compatible electrical signal by one or more selected from a group of DC voltage cancellation, filtration, attenuation, demodulation, modulation, compression, amplification, expansion, digitization, demultiplex, serialization, switching, synchronization, electrical isolation, and impedance matching.

12. The bio sensor interface apparatus of claim 1 further comprising one or more bio sensors that are selected from a group consisting of: a photo plethysmograph, a pulse oximeter, a sphygmomanometer, a thermometer, a pedometer, a capnograph, a respiratory movement sensor, a respiratory flow sensor, a patient movement and orientation sensor, a transdermal blood alcohol sensor and a blood sugar sensor.

13. The bio sensor interface apparatus of claim 1 further comprising at least one connector capable of receiving at least two ECG biosensor signals, wherein the at least two ECG biosensor signals further include a third biosensor signal selected from a group consisting of an electrical signal, a chemical signal, a gas signal, or a force signal.

14. The bio sensor interface apparatus of claim 1 further comprising at least one receiver capable of receiving a wireless biosensor signal.

15. The bio sensor interface apparatus of claim 1 wherein the connectors are one or more selected from a group consisting of: a circular push-pull connector, an ECG AAMI EC-53 connector, a MC PPG connector; a round connector, a screw connector, a rectangular (DIN) connector, a twist coupling connector, a sub-miniature connector, and other industry specified connectors.

16. The bio sensor interface apparatus of claim 1 wherein the power source is within the cell phone and the interface device further includes a power connection to the cell phone.

17. The biosensor interface apparatus of claim 1 further comprising a cell phone processor that computes a physiological measurement corresponding to the electrical signal received from one or more input conductors.

18. The bio sensor interface apparatus of claim 1 further comprising a cell phone audio output device and having the processor configured to communicate the measurement to the audio output device.

19. The bio sensor interface apparatus of claim 1 further comprising a cell phone display with the processor configured to communicate the measurement to the display.

* * * * *